United States Patent
Akasaka

(10) Patent No.: US 10,352,894 B2
(45) Date of Patent: Jul. 16, 2019

(54) LIMITING-CURRENT TYPE GAS SENSOR AND FABRICATION METHOD OF THE SAME, AND SENSOR NETWORK SYSTEM

(71) Applicant: ROHM CO., LTD., Kyoto (JP)

(72) Inventor: Shunsuke Akasaka, Kyoto (JP)

(73) Assignee: ROHM CO., LTD., Kyoto (JP)

( * ) Notice: Subject to any disclaimer, the term of this patent is extended or adjusted under 35 U.S.C. 154(b) by 319 days.

(21) Appl. No.: 15/338,540

(22) Filed: Oct. 31, 2016

(65) Prior Publication Data
US 2017/0122898 A1     May 4, 2017

Related U.S. Application Data

(63) Continuation of application No. PCT/JP2015/059843, filed on Mar. 30, 2015.

(30) Foreign Application Priority Data

May 2, 2014   (JP) ................. 2014-094987

(51) Int. Cl.
    *G01N 27/407*     (2006.01)
    *G01N 27/30*     (2006.01)
    (Continued)

(52) U.S. Cl.
    CPC ....... *G01N 27/4073* (2013.01); *C23C 14/081* (2013.01); *C23C 14/086* (2013.01);
    (Continued)

(58) Field of Classification Search
CPC .. G01M 15/10; G01M 15/102; G01M 15/104; G01N 27/404–407; G01N 27/409; G01N 27/419; G01N 27/41; F02D 41/123; F02D 41/1454; F01N 2560/00–20; F01N 2550/00–24
See application file for complete search history.

(56) References Cited

U.S. PATENT DOCUMENTS 4,487,680 A    12/1984   Logothetis et al.
4,595,485 A *   6/1986   Takahashi .......... G01N 27/4065
                                                  204/192.15
(Continued)

FOREIGN PATENT DOCUMENTS

JP     S57-111441 A     7/1982
JP     S59-166854 A     9/1984
(Continued)

OTHER PUBLICATIONS

Hideaki Takahashi et al., "Thin-film Limiting-current Type Oxygen Sensor", Toyota Central R&D Labs. R&D Review, vol. 27 No. 2 (Jun. 1992).

*Primary Examiner* — Gurpreet Kaur
(74) *Attorney, Agent, or Firm* — Rabin & Berdo, P.C.

(57) ABSTRACT

The limiting-current type gas sensor includes: a porous lower electrode disposed on a substrate; an insulating film disposed on the porous lower electrode; a solid electrolyte layer disposed on the porous lower electrode in an opening formed by patterning the insulating film, and further disposed on the insulating film surrounding the opening; and a porous upper electrode disposed on the solid electrolyte layer, wherein the insulating film realizes non-contact between an edge face of the solid electrolyte layer and the porous lower electrode, in order to suppress the intake of oxygen (O) ion from the edge face of the solid electrolyte layer, and thereby the surface-conduction current component between the porous upper electrode and the porous lower electrode can be reduced. There can be provided the limiting-current type gas sensor capable of reducing the surface-conduction current component and realizing low power consumption.

16 Claims, 33 Drawing Sheets

(51) Int. Cl.
  *C23C 14/08*  (2006.01)
  *C23C 14/10*  (2006.01)
  *C23C 14/34*  (2006.01)
  *G01N 33/00*  (2006.01)

(52) U.S. Cl.
  CPC .............. *C23C 14/10* (2013.01); *C23C 14/34* (2013.01); *G01N 27/304* (2013.01); *G01N 27/4071* (2013.01); *G01N 27/4077* (2013.01); *G01N 33/0016* (2013.01); *G01N 33/0027* (2013.01); *C23C 14/08* (2013.01)

(56) References Cited

U.S. PATENT DOCUMENTS

| | | | |
|---|---|---|---|
| 4,741,817 A * | 5/1988 | Croset | G01N 27/417 |
| | | | 204/425 |
| 2002/0144537 A1 | 10/2002 | Sharp et al. | |
| 2005/0229379 A1 | 10/2005 | Totokawa | |
| 2006/0173579 A1 | 8/2006 | Desrochers et al. | |
| 2006/0173580 A1 | 8/2006 | Desrochers et al. | |
| 2007/0045114 A1 * | 3/2007 | Wang | G01N 27/4074 |
| | | | 204/431 |
| 2010/0206042 A1 * | 8/2010 | Johns | F01N 11/00 |
| | | | 73/23.31 |

FOREIGN PATENT DOCUMENTS

| | | |
|---|---|---|
| JP | H05-312772 A | 11/1993 |
| JP | 2001-056313 A | 2/2001 |
| JP | 2005-504947 A | 2/2005 |
| JP | 2005-300470 A | 10/2005 |
| JP | 2009-298657 A | 12/2009 |

\* cited by examiner

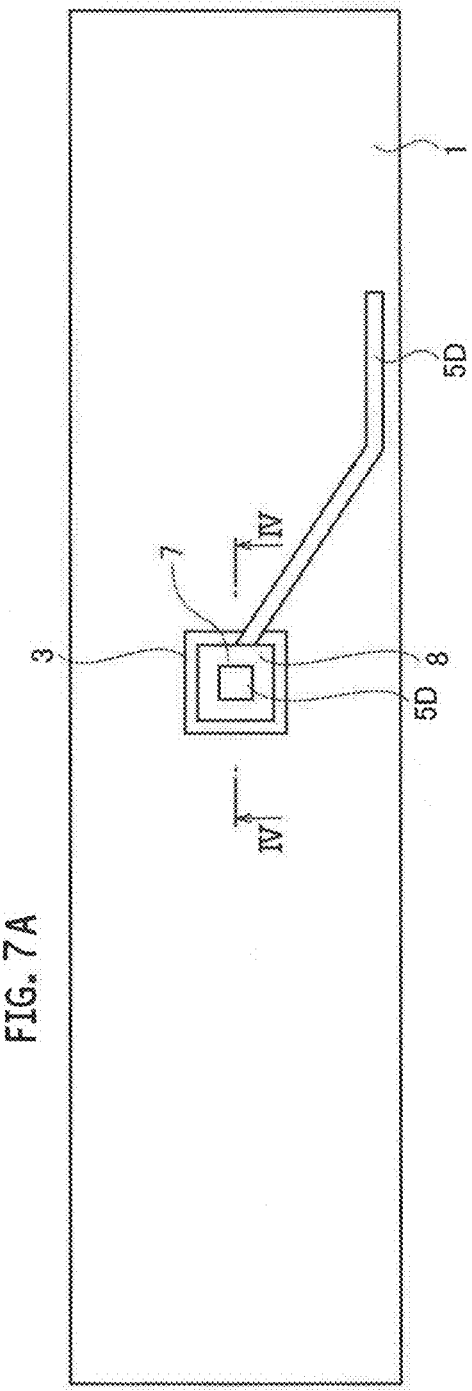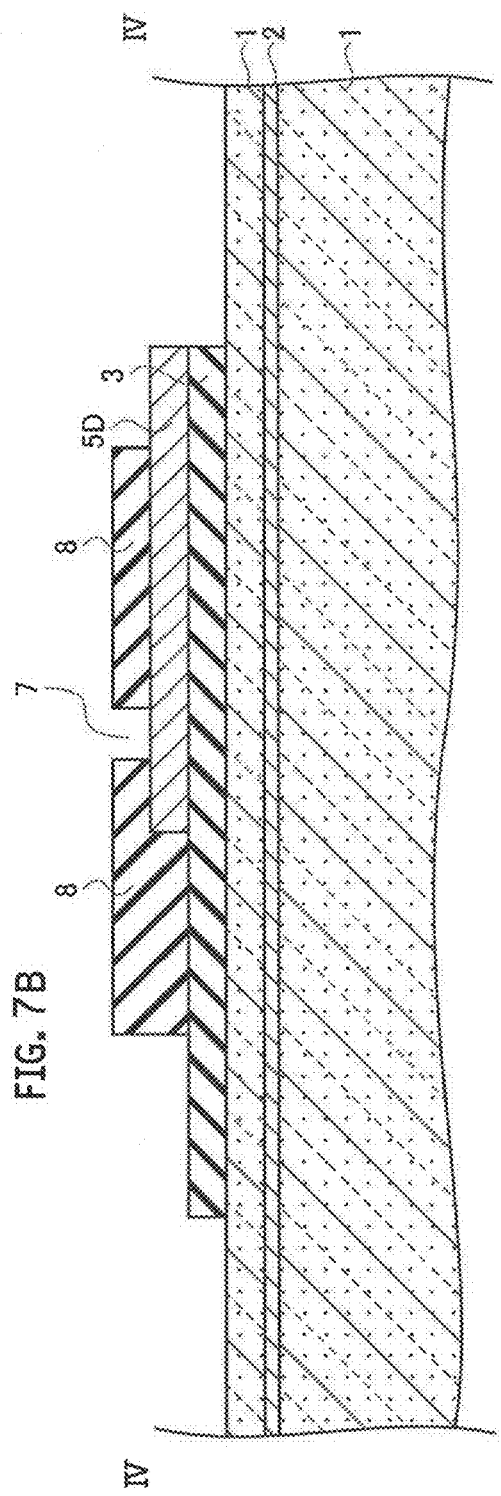
FIG. 7A
FIG. 7B

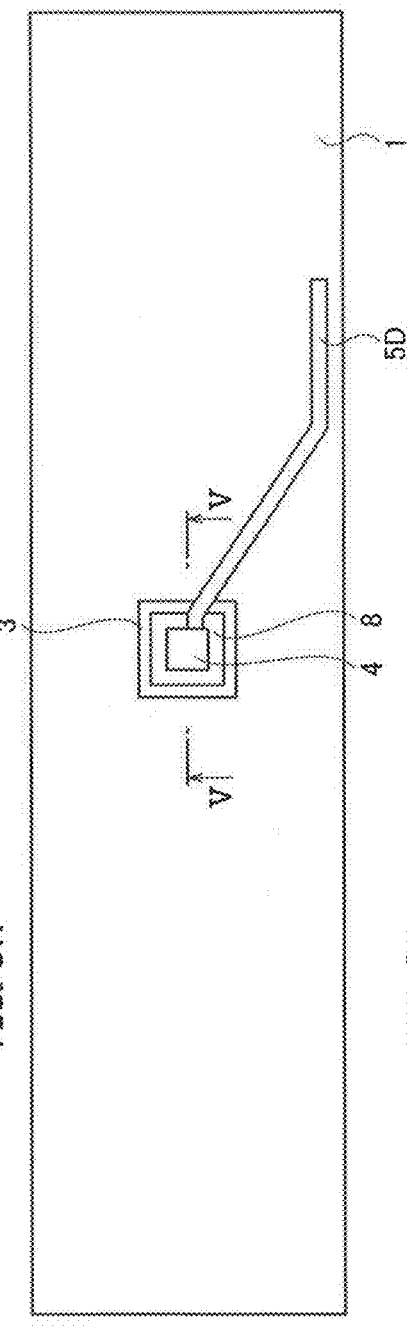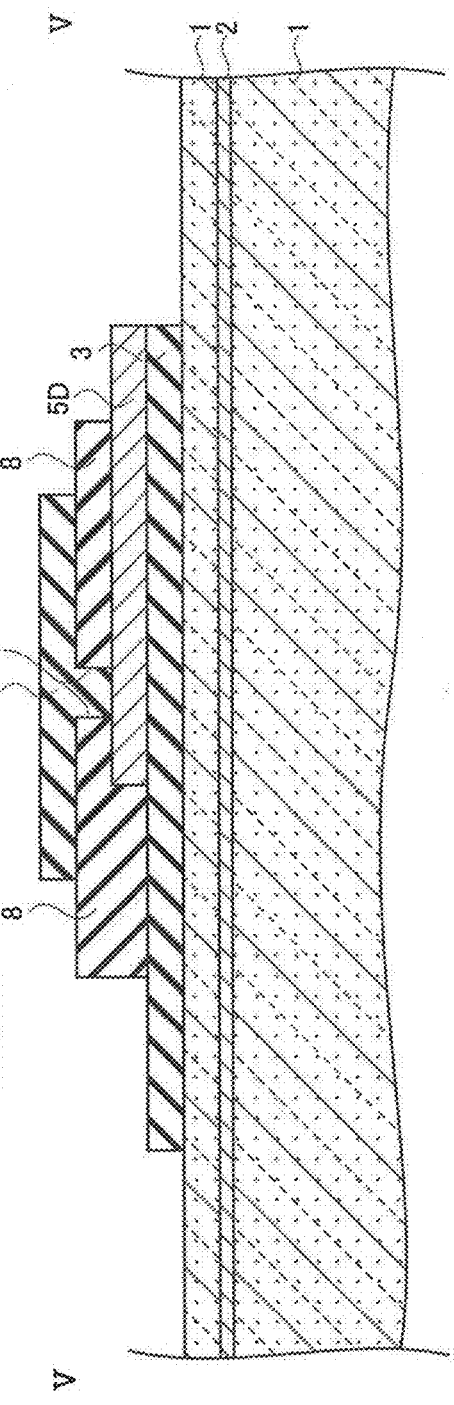

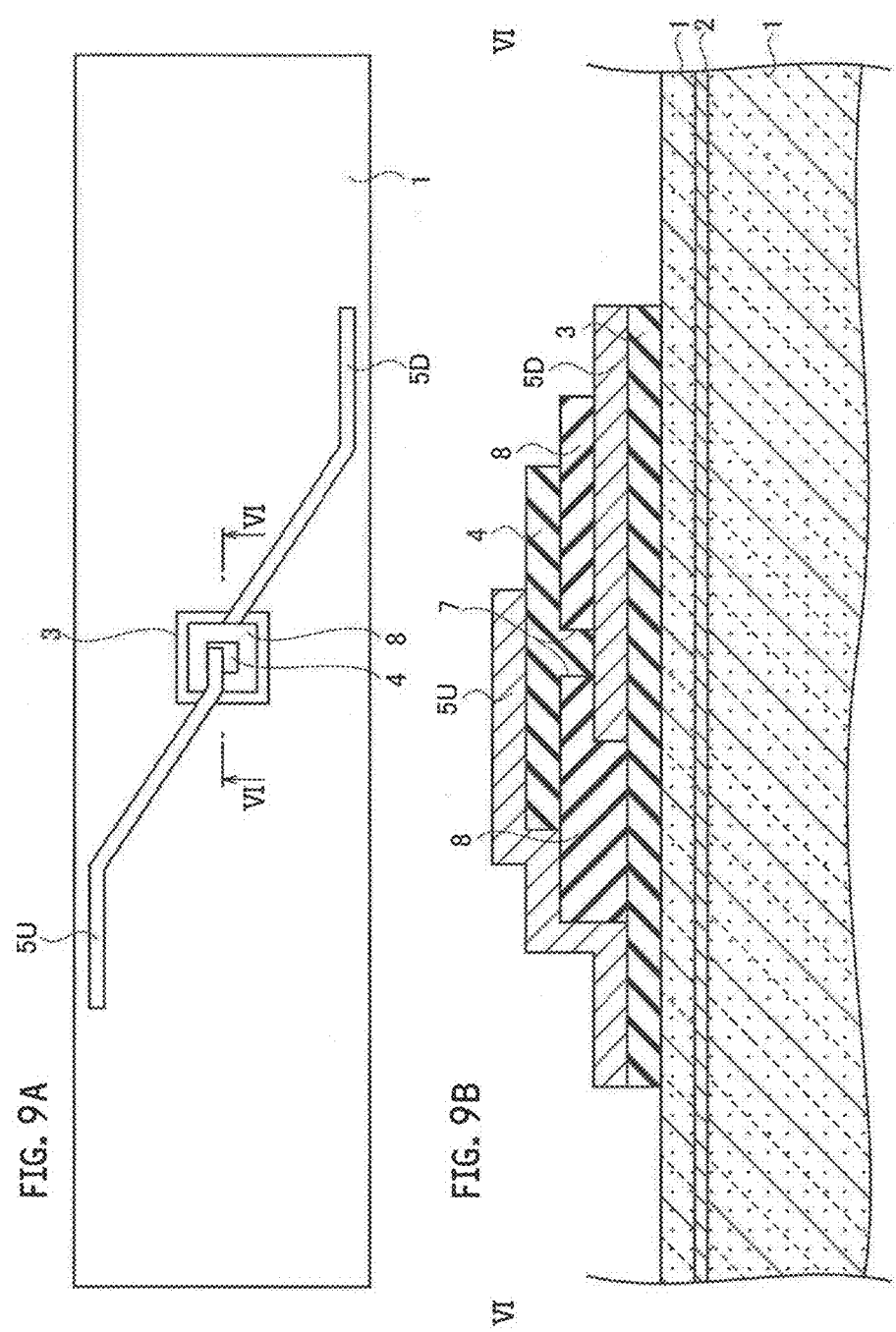

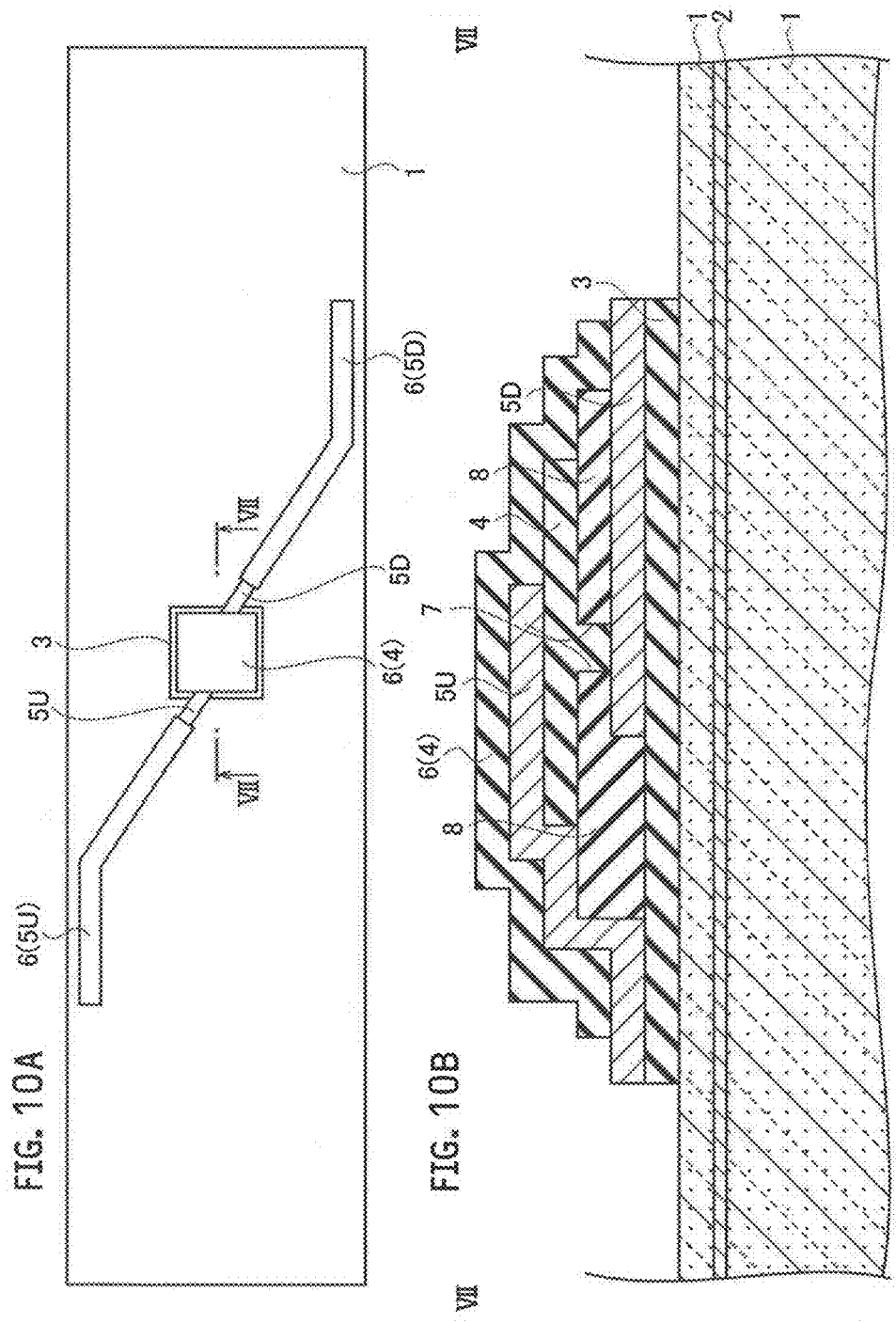

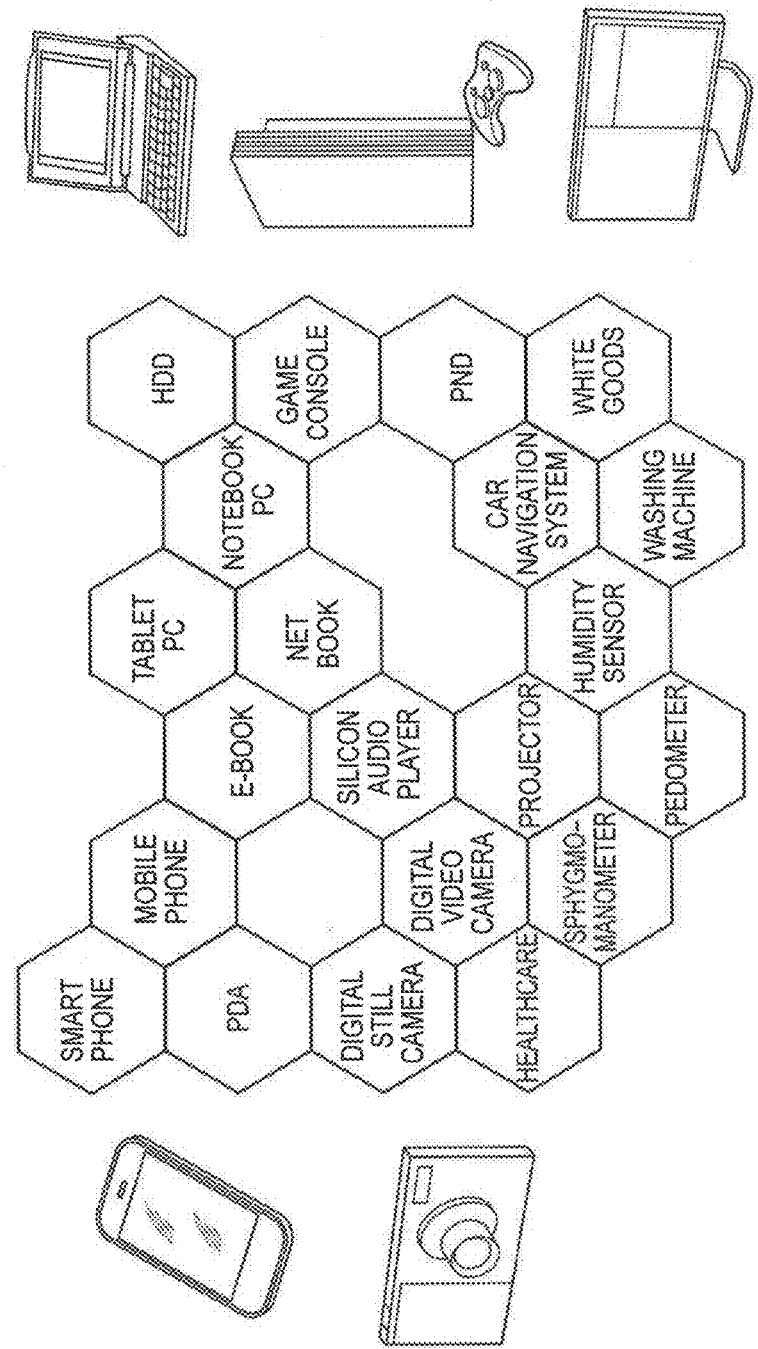

LIMITING-CURRENT TYPE GAS SENSOR AND FABRICATION METHOD OF THE SAME, AND SENSOR NETWORK SYSTEM

CROSS REFERENCE TO RELATED APPLICATIONS

This is a continuation application (CA) of PCT Application No. PCT/JP2015/059843, filed on Mar. 30, 2015, which claims priority to Japan Patent Application No. P2014-094987 filed on May 2, 2014 and is based upon and claims the benefit of priority from prior Japanese Patent Applications No. P2014-094987 filed on May 2, 2014 and PCT Application No. PCT/JP2015/059843, filed on Mar. 30, 2015, the entire contents of each of which are incorporated herein by reference.

FIELD

The embodiments described herein relate to a limiting-current type gas sensor for detecting a predetermined gas density in atmosphere under measurement by a limiting current method, a fabrication method of such a limiting-current type gas sensor, and a sensor network system.

BACKGROUND

Conventionally, resistance change type, capacitance change type, zirconia ($ZrO_2$) solid oxide type humidity sensors, etc. have been known as humidity sensors for detecting a vapor density in measured gas.

There are advantages in which the polymer membrane resistance change type humidity sensors are inexpensive and are easy to from a device. On the other hand, there are disadvantages in which measurement accuracies in low-humidity regions are low, and temperature dependency is large, and elution due to condensation leads to element deteriorations and breakdowns.

Moreover, there are advantages in which the capacitance change type humidity sensors have sufficient linearity, are measurable in whole region of relative humidity, and have small temperature dependency. On the other hand, there is disadvantages in which the capacitance change type humidity sensors have significant effects of waters (tap water etc.) other than a pure water and organic solvents, etc. Moreover, while capacitance in humidity of 0% RH is hundreds of pF, a capacitance change when 1% RH is changed is equal to or less than 1 pF, and therefore periodic calibration is required for exact humidity measurement. While the capacitance change type humidity sensor is an effective device when highly accurate humidity measurement is not required in ordinary office environments, it is unexpected usage in highly accurate humidity measurement, a possible atmosphere of condensation or exposure to gas (for weather observations, or for bathroom), and atmospheres of high temperatures equal to or greater than 100 degrees Celsius (degrees C.). Polymeric materials need to be newly developed to improve durability thereof. While future research and development are expected, novel material developments require many time periods and costs.

There have been commercially available humidity sensors using zirconia solid electrolytes used for humidity measurements in high temperatures. Oxygen sensors using zirconia solid electrolytes have been used for the purpose of improving combustion efficiencies of automobiles, and reduction of $NO_x$, and there is sufficient results for durability as materials. However, since the temperature of zirconia is increased to hundreds of degrees C. when using it, power consumption is as high as 100 W, and handling of high-temperature substance is still more difficult, its mart is limited to apart of industrial uses.

Consequently, in recent years, attention is being given to limiting-current type sensors using zirconia thin film. Such a kind of the limiting-current type oxygen sensor has an advantages of high reliability and sufficient linearity.

SUMMARY

In the embodiment, it has been found out since a surface-conduction current is increased by intake of oxygen (O) ion from an edge face, in a limiting-current type gas sensor, and thereby reducing sensor sensitivity in accordance with increase of a leakage current between main electrodes (anode and cathode).

The embodiment provides: a limiting-current type gas sensor capable of reducing a surface-conduction current component and realizing low power consumption; a fabrication method of such a limiting-current type gas sensor; and a sensor network system.

According to one aspect of the embodiment, there is provided a limiting-current type gas sensor comprising: a substrate; a porous lower electrode disposed on the substrate; an insulating film disposed on the porous lower electrode; a solid electrolyte layer disposed on the porous lower electrode in an opening formed by patterning the insulating film, and further disposed on the insulating film surrounding the opening; and a porous upper electrode disposed on the solid electrolyte layer so as to be opposite to the porous lower electrode, and so as to be disposed in a substantially vertical direction with respect to the substrate, wherein the insulating film realizes non-contact between an edge face of the solid electrolyte layer and the porous lower electrode, in order to suppress the intake of oxygen (O) ion from the edge face of the solid electrolyte layer, and thereby the surface-conduction current component between the porous upper electrode and the porous lower electrode can be reduced.

According to another aspect of the embodiment, there is provided a fabrication method of a limiting-current type gas sensor, the fabrication method comprising: forming a porous lower electrode on a substrate; forming an insulating film on the porous lower electrode; patterning the insulating film in order to form an opening; forming a solid electrolyte layer on the porous lower electrode in the opening and on the insulating film surrounding the opening; and forming a porous upper electrode on the solid electrolyte layer so as to be opposite to the porous lower electrode, and so as to be disposed in a substantially vertical direction with respect to the substrate, wherein the insulating film realizes non-contact between an edge face of the solid electrolyte layer and the porous lower electrode, in order to suppress the intake of oxygen (O) ion from the edge face of the solid electrolyte layer, and thereby the surface-conduction current component between the porous upper electrode and the porous lower electrode can be reduced.

According to still another aspect of the embodiment, there is provided a sensor network system comprising the above-mentioned limiting-current type gas sensor According to the embodiment, there can be provided: the limiting-current type gas sensor capable of reducing the surface-conduction current component and realizing low power consumption; the fabrication method of such a limiting-current type gas sensor; and the sensor network system.

BRIEF DESCRIPTION OF DRAWINGS

FIG. 7A is a schematic plan view showing a process of the fabrication method of the limiting-current type gas sensor according to the first embodiment (Phase 3).

FIG. 7B is a schematic cross-sectional structure diagram taken in the line IV-IV of FIG. 7A.

FIG. 8A is a schematic plan view showing a process of the fabrication method of the limiting-current type gas sensor according to the first embodiment (Phase 4).

FIG. 8B is a schematic cross-sectional structure diagram taken in the line V-V of FIG. 8A.

FIG. 9A is a schematic plan view showing a process of the fabrication method of the limiting-current type gas sensor according to the first embodiment (Phase 5).

FIG. 9B is a schematic cross-sectional structure diagram taken in the line VI-VI of FIG. 9A.

FIG. 10A is a schematic plan view showing a process of the fabrication method of the limiting-current type gas sensor according to the first embodiment (Phase 6).

FIG. 10B is a schematic cross-sectional structure diagram taken in the line VII-VII of FIG. 10A.

FIG. 37 is a schematic block configuration diagram showing a sensor network to which the limiting-current type gas sensor according to the embodiments is applied.

DESCRIPTION OF EMBODIMENTS

Figure 1A:
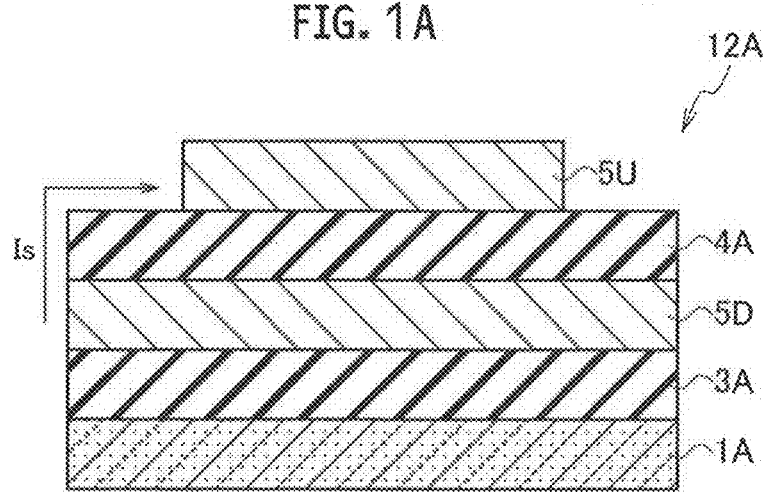
FIG. 1A is a schematic cross-sectional structure diagram showing a sensor portion of a limiting-current type gas sensor according to a comparative example.

Next, the embodiments will be described with reference to drawings. In the description of the following drawings, the identical or similar reference numeral is attached to the identical or similar part. However, it should be noted that the drawings are schematic and therefore the relation between thickness and the plane size and the ratio of the thickness differs from an actual thing. Therefore, detailed thickness and size should be determined in consideration of the following explanation. Of course, the part from which the relation and ratio of a mutual size differ also in mutually drawings is included.

Moreover, the embodiments shown hereinafter exemplify the apparatus and method for materializing the technical idea; and the embodiments do not intend to specify the material, shape, structure, placement, etc. of component part(s) as the following. The embodiments may be changed without departing from the spirit or scope of claims.

First Embodiment (Limiting-Current Type Gas Sensor)

Figure 1B:
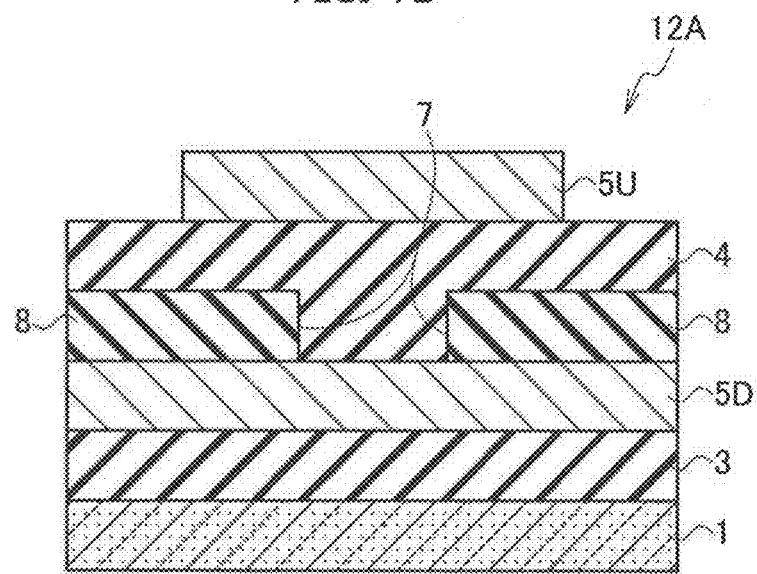
FIG. 1B is a schematic cross-sectional structure diagram showing a sensor portion of a limiting-current type gas sensor according to the first embodiment.

FIG. 1A shows a schematic cross-sectional structure of a sensor portion of a limiting-current type gas sensor 12A according to a comparative example, and FIG. 1B shows a schematic cross-sectional structure of a sensor portion of a limiting-current type gas sensor 12 according to a first embodiment.

As shown in FIG. 1A, the limiting-current type gas sensor 12A according to the comparative example includes: a substrate 1A; an insulating film 3A disposed on the substrate 1A; a porous lower electrode 5D disposed on the insulating film 3A; a solid electrolyte layer 4A disposed on the porous lower electrode 5D; and a porous upper electrode 5U disposed on the solid electrolyte layer 4A.

In the limiting-current type gas sensor 12A according to the comparative example, as shown in FIG. 1A, detection sensitivity is reduced due to generation of a surface-conduction current $I_S$ component between the porous upper electrode 5U and the porous lower electrode 5D, due to intake of oxygen (O) ion from an edge face of the solid electrolyte layer.

As shown in FIG. 1B, the limiting-current type gas sensor 12 according to embodiments includes: a substrate 1; a porous lower electrode 5D disposed on the substrate 1; an insulating film 8 disposed on the porous lower electrode 5D; a solid electrolyte layer 4 disposed on the porous lower electrode 5D in an opening 7 formed by patterning the insulating film 8, and further disposed on the insulating film 8 surrounding the opening 7; and; and a porous upper electrode 5U disposed on the solid electrolyte layer 4 so as to be opposite to the porous lower electrode 5D, and so as to be disposed in a substantially vertical direction with respect to the substrate 1.

In the limiting-current type gas sensor 12 according to the embodiments, as shown in FIG. 1B, the insulating film 8 realizes non-contact between an edge face of the solid electrolyte layer 4 and the porous lower electrode 5D, in order to suppress the intake of oxygen (O) ion from the edge face of the solid electrolyte layer 4, and thereby the surface-conduction current component between the porous upper electrode 5U and the porous lower electrode 5D can be reduced.

Moreover, the limiting-current type gas sensor 12 may include a gas intake film 3 disposed on the substrate 1, and the porous lower electrode 5D may be disposed on the gas intake film 3.

Figure 2:
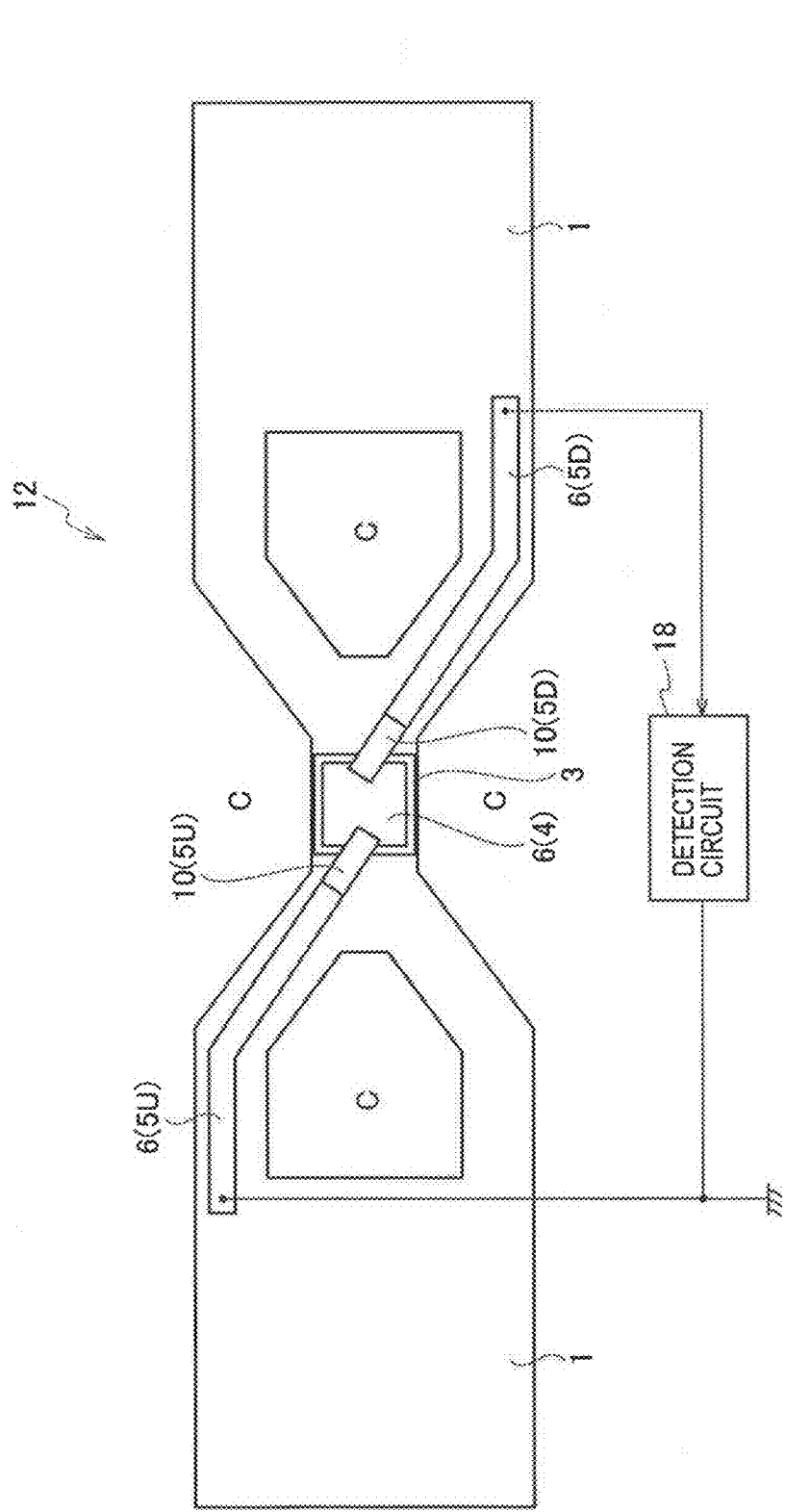
FIG. 2 is a schematic planar pattern configuration diagram showing the limiting-current type gas sensor according to the first embodiment.
Figure 3:
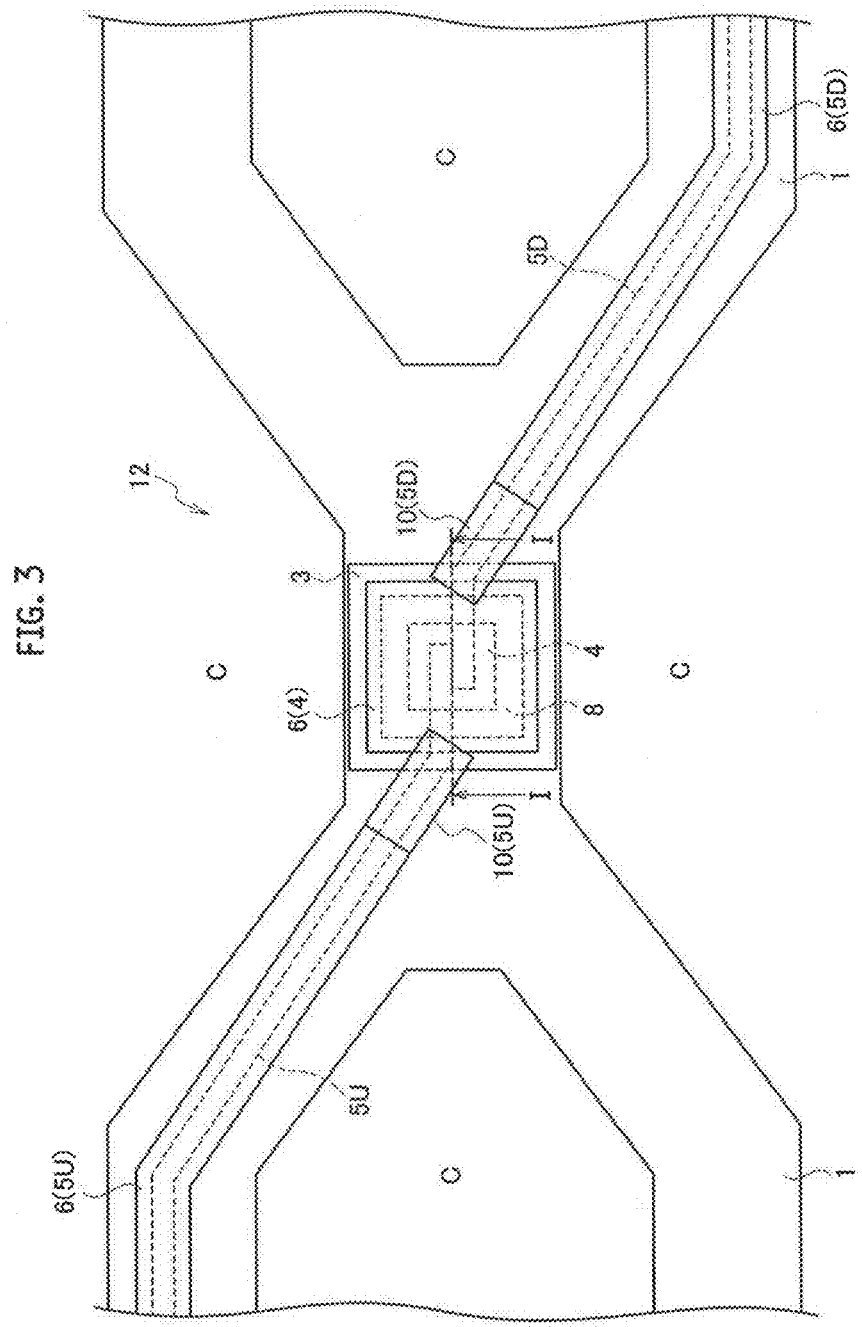
FIG. 3 is a schematic planar pattern configuration diagram showing an enlarged sensor portion of the limiting-current type gas sensor according to the first embodiment.
Figure 4:
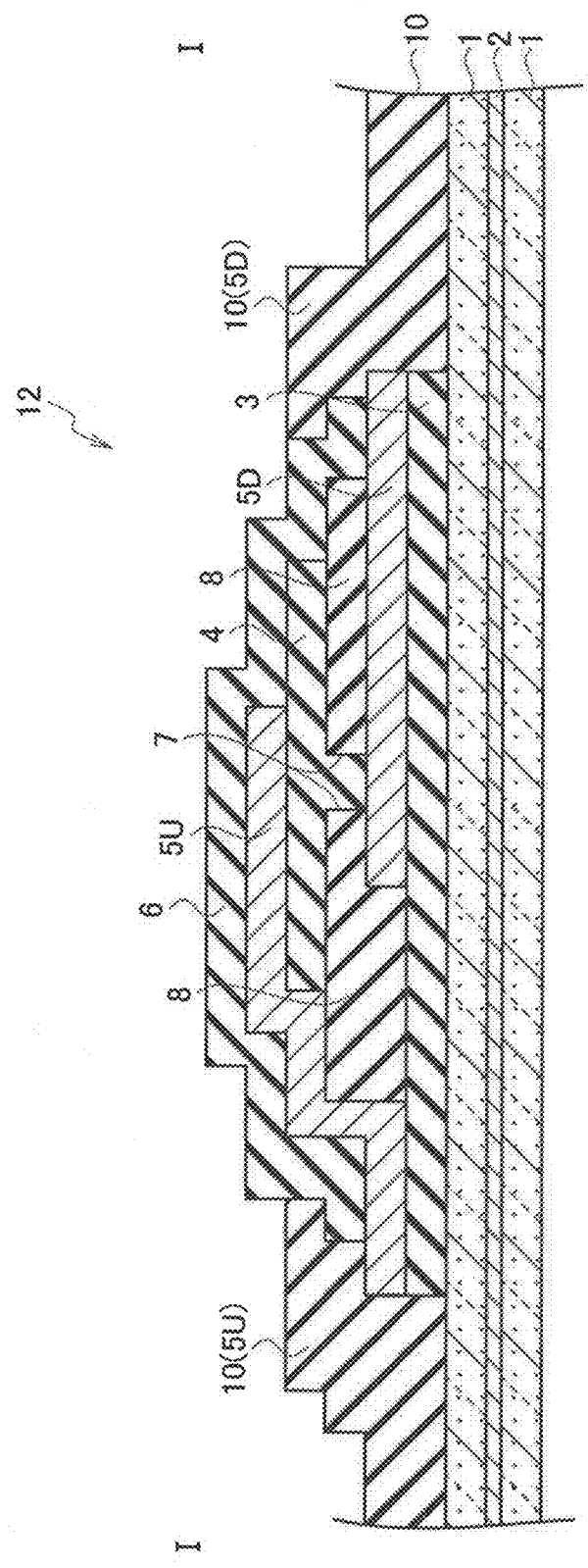
FIG. 4 is a schematic cross-sectional structure diagram taken in the line I-I of FIG. 3.

FIG. 2 shows a schematic planar pattern configuration of a limiting-current type gas sensor 12 according to the first embodiment, FIG. 3 shows a schematic planar pattern configuration of an enlarged sensor portion thereof, and FIG. 4 shows a schematic cross-sectional structure taken in the line I-I of FIG. 3.

As shown in FIGS. 2-4, the limiting-current type gas sensor 12 according to the first embodiment includes: a substrate 1; a porous lower electrode 5D disposed on the substrate 1; an insulating film 8 disposed on the porous lower electrode 5D; a solid electrolyte layer 4 disposed on the porous lower electrode 5D in an opening 7 formed by patterning the insulating film 8, and further disposed on the insulating film 8 surrounding the opening 7; and a porous upper electrode 5U disposed on the solid electrolyte layer 4 so as to be opposite to the porous lower electrode 5D, and so as to be disposed in a substantially vertical direction with respect to the substrate 1.

In this case, the insulating film 8 realizes non-contact between the edge face of the solid electrolyte layer 4 and the porous lower electrode 5D, in order to suppress the intake of oxygen (O) ion from the edge face of the solid electrolyte layer 4, and thereby the surface-conduction current component between the porous upper electrode 5U and the porous lower electrode 5D can be reduced.

Moreover, as shown in FIG. 2, the limiting-current type gas sensor 12 according to the first embodiment includes a detection circuit 18 configured to detect a predetermined gas density in measured gas with a limiting current method by applying voltage between the porous upper electrode 5U and the porous lower electrode 5D. In the present embodiment, the detection circuit 18 can detect the oxygen density on the basis of a limiting current. Moreover, the detection circuit 18 can detect vapor density on the basis of the limiting current.

As shown in FIGS. 2-4, the limiting-current type gas sensor 12 according to the first embodiment may include: a first low-thermal expansion film 6 (5U) for stress relaxation disposed on the porous upper electrode 5U; a second low-thermal expansion film 6(5D) for stress relaxation disposed on the porous lower electrode 5D; and a third low-thermal expansion film 6(4) for stress relaxation disposed on the solid electrolyte layer 4.

As shown in FIGS. 2-4, the limiting-current type gas sensor 12 according to the first embodiment may include: a first porous insulating film 10(5U) for suppressing warpage disposed on the porous upper electrode 5U so as to extend over between the first low-thermal expansion film 6(5U) for stress relaxation and the third low-thermal expansion film 6(4) for stress relaxation in a planar view; and a second porous insulating film 10 (5D) for suppressing warpage disposed on the porous lower electrode 5D so as to extend over between the second low-thermal expansion film 6 (5D) for stress relaxation and the third low-thermal expansion film 6(4) for stress relaxation in a planar view.

As shown in FIGS. 2-4, the limiting-current type gas sensor 12 according to the first embodiment includes a Micro Electro Mechanical Systems (MEMS) element structure having both-ends-supported beam structure (straddle-mounted beam structure) as fundamental structure. Although the detailed structure is mentioned below, a sensor portion is disposed at a center portion, the porous lower electrode 5D and porous upper electrode 5U, connected to the sensor portion, are disposed at a beam portion of the both-ends-supported beam structure (straddle-mounted beam structure), and the detection circuit 18 is connected between the porous lower electrode 5D and the porous upper electrode 5U.

A micro heater 2 for heating the sensor portion is embedded in the sensor portion at the center portion, and the MEMS element structure having both-ends-supported beam structure (straddle-mounted beam structure) is applied as the fundamental structure, and thereby the heat capacity of the sensor portion at the center portion is reduced, and the sensor sensitivity can be improved.

In the limiting-current type gas sensor 12 according to the first embodiment, the substrate 1 includes the micro heater 2, as shown in FIG. 4. The micro heater 2 may be disposed on an upper portion of the substrate 1 or a lower portion of the substrate 1. Moreover, the micro heater 2 may be embedded in the inside of the substrate 1, as shown in FIG. 4. The micro heater 2 can be formed including a Pt heater formed by printing or a polysilicon heater, for example. Moreover, a laminated film 100 including a silicon oxide film/silicon nitride film including the micro heater 2 formed with polysilicon may be formed on the surface of the substrate 1 (FIG. 21).

The porous lower electrode 5D and the porous upper electrode 5U can be formed including a porous Pt electrode. The porous Pt electrode can be formed by printing, vacuum evaporation, or sputtering. The thickness of the porous lower electrode 5D and porous upper electrode 5U is within a range from approximately 0.5 µm to approximately 10 µm, for example.

The insulating film 8 can be formed including any one of $Al_2O_3$, $Al_2O_3$—$SiO_2$, YSZ—$SiO_2$ or YSZ—$Al_2O_3$. The insulating film 8 can be formed by a printing process or sputtering process. The thickness of the insulating film 8 is within a range from approximately 1.0 µm to approximately 10 µm, for example. The YSZ described herein is an Yttria-Stabilized Zirconia (YSZ) film.

By forming the insulating film 8, a contact area between the stabilized zirconia (4) and the porous Pt lower electrode (5D) can be stabilized, contact of the edge face of the stabilized zirconia (4) to the porous Pt lower electrode (5D) is eliminated, and the surface conduction component between the porous Pt lower electrode (5D) and the porous Pt upper electrode (5U) can be removed.

The solid electrolyte layer 4 can be formed including a stabilized zirconia film in which at least one of YSZ, YSZ—$SiO_2$, or YSZ—$Al_2O_3$ is contained. The solid electrolyte layer 4 can be formed by a printing process or sputtering process. The thickness of the solid electrolyte layer 4 is with a range from approximately 1.0 µm to approximately 10 µm, for example.

A film density of the low-thermal expansion film 6 for stress relaxation can be adjusted in accordance with a gas volume to be detected.

Moreover, the low-thermal expansion film 6 for stress relaxation can be formed including any one of a dense film, porous film, or composite film of the dense film and the porous film.

Moreover, the low-thermal expansion film 6 for stress relaxation may be formed including materials containing at least one of $SiO_2$, $Al_2O_3$, YSZ, or mullite. Moreover, the low-thermal expansion film 6 for stress relaxation can be formed by a printing process or sputtering process. The thickness of the low-thermal expansion film 6 for stress relaxation is within a range from approximately 1.0 µm to approximately 5.0 µm, for example.

The porous insulating film 10 for suppressing warpage may be formed including materials containing at least one of $SiO_2$, $Al_2O_3$, YSZ, or mullite. Moreover, the porous insulating film 10 for suppressing warpage can be formed by a printing process or sputtering process. The thickness of the porous insulating film 10 for suppressing warpage is within a range from approximately 1.0 µm to approximately 5.0 µm, for example.

Moreover, the substrate 1 may have MEMS beam structure, in the limiting-current type gas sensor 12 according to the first embodiment. The substrate 1 can be formed including an Si substrate of which the thickness is equal to or less than 10 µm, or preferably equal to or less than 2 µm. It is possible to reduce power consumption in the micro heater 2 since the thickness L of the Si substrate 1 can be reduced to equal to or less than 2 µm if the MEMS is applied thereto, and thereby the heat capacity becomes small.

Moreover, the limiting-current type gas sensor 12 according to the first embodiment is formed as both-ends-supported beam structure on a cavity area C formed in the substrate 1, as shown in FIGS. 2-4. The both-ends-supported beam structure body is a both-ends-supported beam structure body, formed of the MEMS, of which the thickness is equal to or less than 10 µm, or preferably equal to or less than 2 µm.

Moreover, the limiting-current type gas sensor 12 may include a gas intake film 3 disposed on the substrate 1, and the porous lower electrode 5D may be disposed on the gas intake film 3.

The gas intake film 3 can be formed including a porous film containing any one of $Al_2O_3$, $Al_2O_3$—$SiO_2$, YSZ—$SiO_2$, or YSZ—$Al_2O_3$. The gas intake film 3 can be formed by a printing process or sputtering process. In the present embodiment, the thickness of the gas intake film 3 is within a range from approximately 0 µm to approximately 10 µm, for example. Accordingly, it is not necessary to always include the gas intake film 3. In that case, the porous lower electrode 5D and the porous upper electrode 5U which can be formed including a porous Pt electrode can be utilized as the gas intake film. Such a limiting-current type gas sensor may be fabricated by methods other than MEMS. The thickness of the Si substrate 1 is approximately 600 μm, for example. Other configurations are the same as those of FIG. 1.

(Fabrication Method)

As shown in FIGS. 5-9, a fabrication method of the limiting-current type gas sensor according to the first embodiment includes: forming a porous lower electrode 5D on a substrate 1; forming an insulating film 8 on the porous lower electrode 5D; patterning the insulating film 8 in order to form an opening 7; forming a solid electrolyte layer 4 on the porous lower electrode 5D in the opening 7 and on the insulating film 8 surrounding the opening 7; and forming a porous upper electrode 5U on the solid electrolyte layer 4 so as to be opposite to the porous lower electrode 5D, and so as to be disposed in a substantially vertical direction with respect to the substrate 1. In this case, the insulating film 8 realizes non-contact between the edge face of the solid electrolyte layer 4 and the porous lower electrode 5D, in order to suppress the intake of oxygen (O) ion from the edge face of the solid electrolyte layer 4, and thereby the surface-conduction current component between the porous upper electrode 5U and the porous lower electrode 5D can be reduced.

Moreover, as shown in FIG. 10, the fabrication method of the limiting-current type gas sensor according to the first embodiment further includes forming a first low-thermal expansion film 6 (5U) for stress relaxation on the porous upper electrode 5U, forming a second low-thermal expansion film 6 (5D) for stress relaxation on the porous lower electrode 5D, and forming a third low-thermal expansion film 6(4) for stress relaxation on the solid electrolyte layer 4.

Moreover, as shown in FIG. 11, the fabrication method of the limiting-current type gas sensor according to the first embodiment further includes: forming a first porous insulating film 10(5U) for suppressing warpage on the porous upper electrode 5U so as to extend over between the first low-thermal expansion film 6(5U) for stress relaxation and the third low-thermal expansion film 6(4) for stress relaxation in a planar view; and forming a second porous insulating film 10 (5D) for suppressing warpage on the porous lower electrode 5D so as to extend over between the second low-thermal expansion film 6 (5D) for stress relaxation and the third low-thermal expansion film 6(4) for stress relaxation in a planar view.

Figure 12:
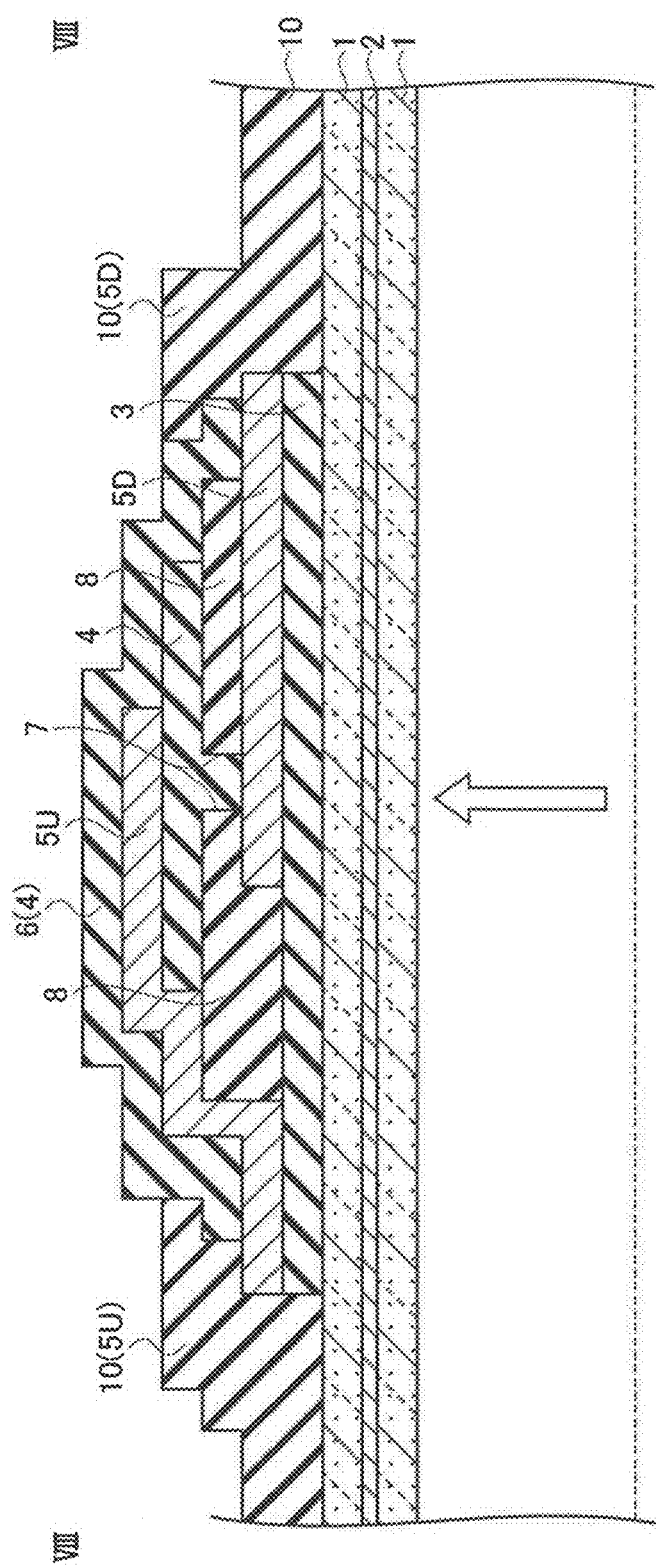
FIG. 12 is a schematic cross-sectional structure diagram showing a process of the fabrication method of the limiting-current type gas sensor according to the first embodiment (Phase 8).

Moreover, as shown in FIG. 12, the fabrication method of the limiting-current type gas sensor according to the first embodiment further includes forming both-ends-supported beam structure on a cavity formed in the substrate 1 by etching the substrate 1.

Moreover, the fabrication method of the limiting-current type gas sensor according to the first embodiment may include forming a micro heater 2 on an upper portion of the substrate 1 or a lower portion of the substrate 1.

Moreover, the fabrication method of the limiting-current type gas sensor according to the first embodiment may include forming the micro heater 2 embedded to an inside of the substrate 1.

Moreover, the fabrication method of the limiting-current type gas sensor according to the first embodiment may include forming a gas intake film 3 on the substrate 1, and may form the porous lower electrode 5D on the gas intake film 3.

Moreover, in the fabrication method of the limiting-current type gas sensor according to the first embodiment, the micro heater 2, the gas intake film, the porous lower electrode, the porous upper electrode, the insulating film, the solid electrolyte layer, a low-thermal expansion film for stress relaxation, and the porous insulating film for suppressing warpage can be formed by a printing process.

The fabrication method of the limiting-current type gas sensor according to the first embodiment will now be explained with reference to FIGS. 5-12.

Figure 5A:
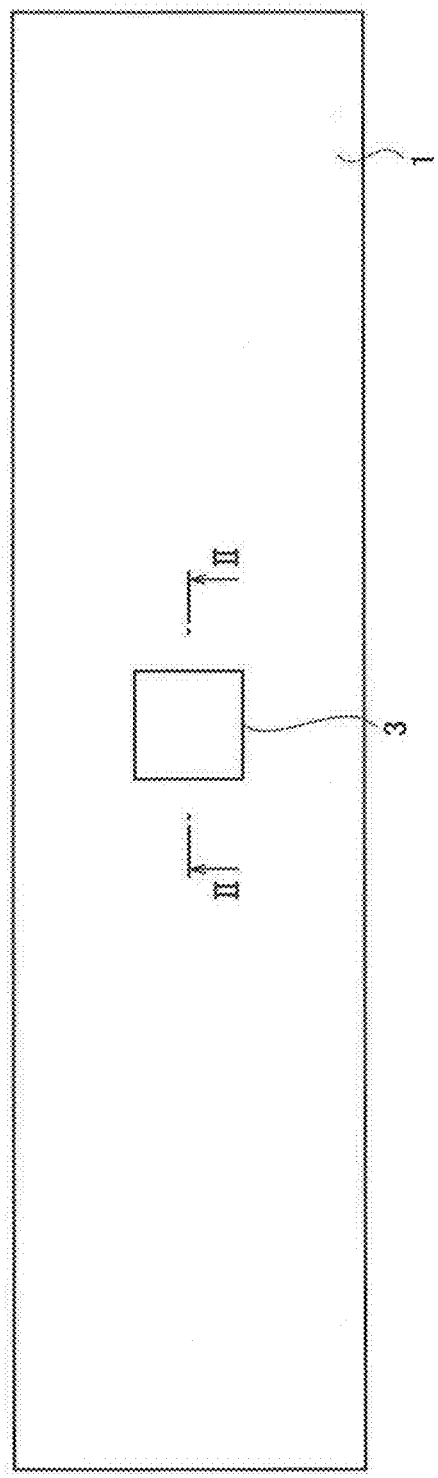
FIG. 5A is a schematic plan view diagram showing a process of a fabrication method of the limiting-current type gas sensor according to the first embodiment (Phase 1).
Figure 5B:
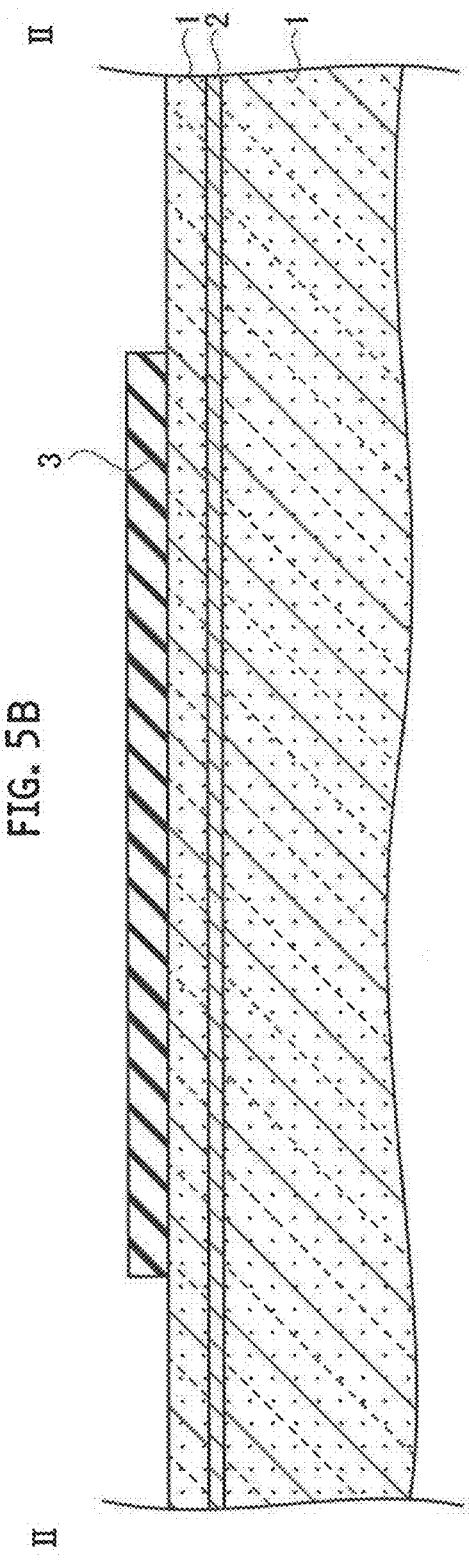
FIG. 5B is a schematic cross-sectional structure diagram taken in the line II-II of FIG. 5A.

(a) Firstly, as shown in FIGS. 5A and 5B, the gas intake film 3 is formed on the substrate 1 in which the micro heater 2 is embedded. Since the gas intake film 3 disclosed herein is a porous film, it serves as a passage way of gas. Formation of the gas intake film 3 may be omitted.

Figure 6A:
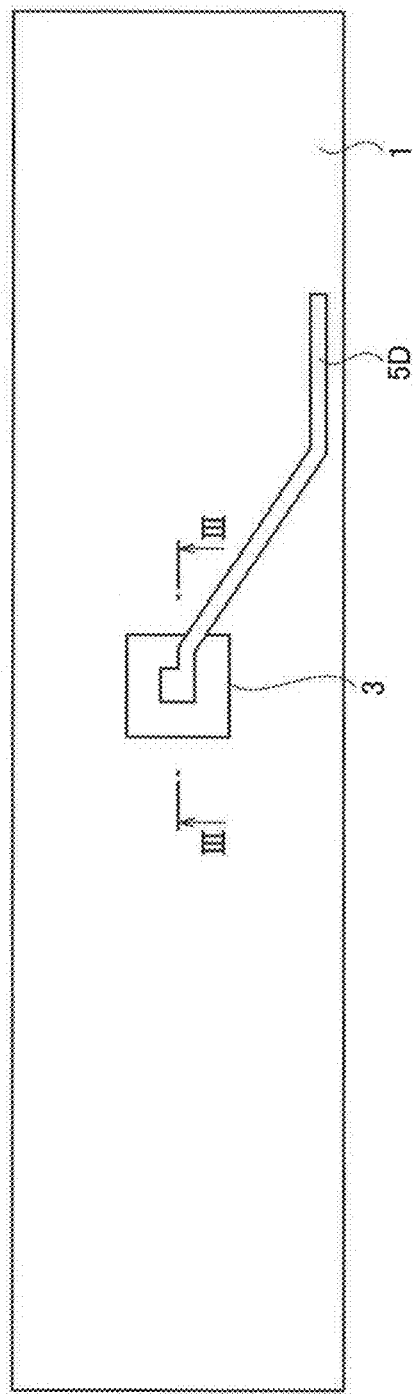
FIG. 6A is a schematic plan view showing a process of the fabrication method of the limiting-current type gas sensor according to the first embodiment (Phase 2).
Figure 6B:
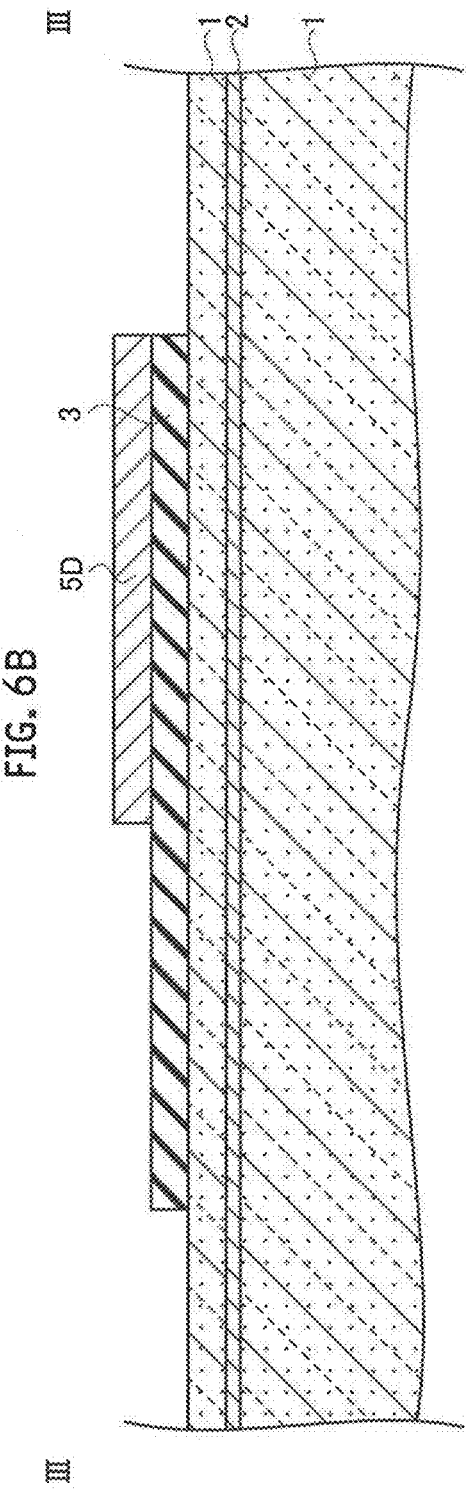
FIG. 6B is a schematic cross-sectional structure diagram taken in the line of FIG. 6A.

(b) Next, as shown in FIGS. 6A and 6B, the porous lower electrode 5D is formed on the gas intake film 3 and the substrate 1. Since the porous lower electrode 5D is formed including a porous Pt electrode, for example, it may be configured to pass the gas through an inside of the porous Pt electrode.

(c) Next, as shown in FIGS. 7A and 7B, after forming the insulating film 8 on the porous lower electrode 5D, the insulating film 8 is patterned in order to form the opening 7. In the present embodiment, by forming the insulating film 8, a contact area between the stabilized zirconia (4) and the porous Pt lower electrode (5D) can be stabilized, contact of the edge face of the stabilized zirconia (4) to the porous Pt lower electrode (5D) is eliminated, and the surface conduction component between the porous Pt lower electrode (5D) and the porous Pt upper electrode (5U) can be removed.

(d) Next, as shown in FIGS. 8A and 8B, the solid electrolyte layer 4 is formed on the porous lower electrode 5U in the opening 7, and on the insulating film 8 surrounding the opening 7. The solid electrolyte layer 4 is formed including Yttria-Stabilized Zirconia (YSZ), for example, in the present embodiment.

(e) Next, as shown in FIGS. 9A and 9B, the porous upper electrode 5U is formed on the solid electrolyte layer 4 so as to be opposite to the porous lower electrode 5D and so as to be disposed in a substantially vertical direction with respect to the substrate 1. The porous upper electrode 5U is formed so as to be extended over the insulating film 8, the gas intake film 3, and the substrate 1, as shown in FIG. 9A. The porous upper electrode 5U is formed including a porous Pt electrode, for example.

(f) Next, as shown in FIGS. 10A and 10B, the first low-thermal expansion film 6(5U) for stress relaxation is formed on the porous upper electrode 5U, the second low-thermal expansion film 6(5D) for stress relaxation is formed on the porous lower electrode 5D, and the third low-thermal expansion film 6(4) for stress relaxation is formed on the solid electrolyte layer 4. A film density of the low-thermal expansion film 6 for stress relaxation can be adjusted in accordance with a gas volume to be detected. Moreover, the low-thermal expansion film 6 for stress relaxation can be formed including any one of a dense film, porous film, or composite film of the dense film and the porous film. Moreover, the low-thermal expansion film 6 for stress relaxation is formed including materials containing at least one of $SiO_2$, $Al_2O_3$, YSZ, or mullite. Moreover, the low-thermal expansion film 6 for stress relaxation can be formed by a printing process or sputtering process. Since the low-thermal expansion film 6 for stress relaxation is an insulating film having a low thermal expansion coefficient, a stress at the time of heating can be relaxed by forming the low-thermal expansion film 6 for stress relaxation.

Figure 11A:
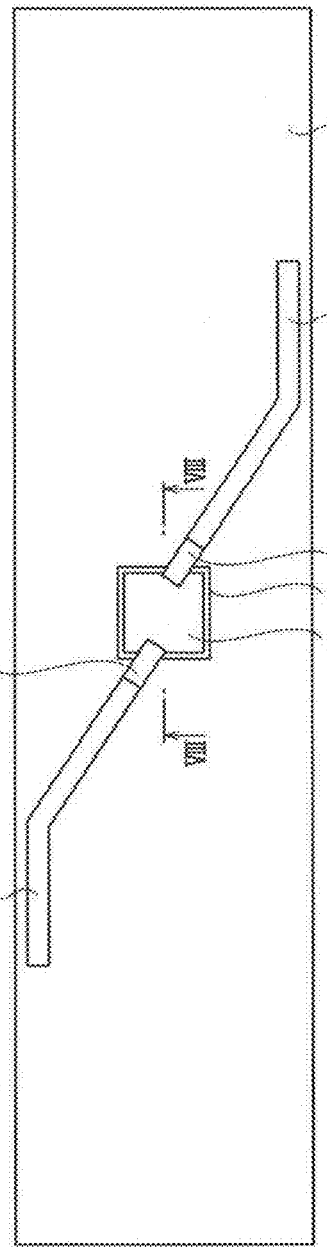
FIG. 11A is a schematic plan view showing a process of the fabrication method of the limiting-current type gas sensor according to the first embodiment (Phase 7).
Figure 11B:
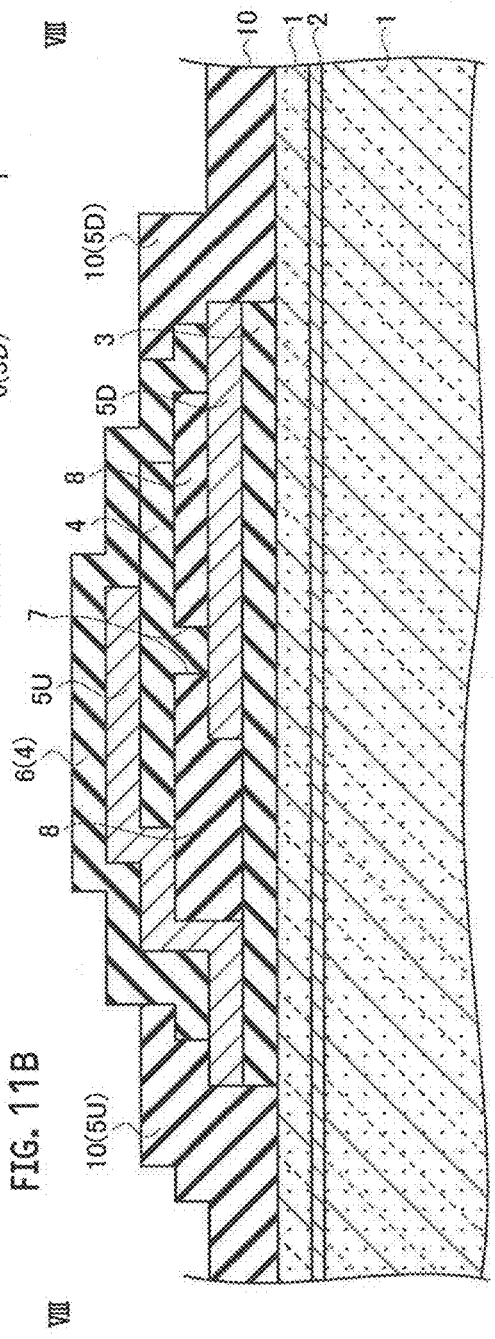
FIG. 11B is a schematic cross-sectional structure diagram taken in the line VIII-VIII of FIG. 11A.

(g) Next, as shown in FIGS. 11A and 11B, the first porous insulating film 10 (5U) for suppressing warpage is formed on the porous upper electrode 5U so as to extend over between the first low-thermal expansion film 6 (5U) for stress relaxation and the third low-thermal expansion film 6(4) for stress relaxation in a planar view, and the second porous insulating film 10 (5D) for suppressing warpage is formed on the porous lower electrode 5D so as to extend over between the second low-thermal expansion film 6(5D) for stress relaxation and the third low-thermal expansion film 6(4) for stress relaxation in a planar view. The porous insulating film 10 for suppressing warpage is formed including materials containing at least one of $SiO_2$, $Al_2O_3$, YSZ, or mullite. Moreover, the porous insulating film 10 for suppressing warpage can be formed by a printing process or sputtering process. By forming the porous insulating film 10 for suppressing warpage, a warpage of the beam structure at the time of heating can be reduced, and durability can be improved.

(h) Next, as shown in FIG. 12, the substrate 1 is etched in the arrow direction from the back side surface. As a result, as shown in FIGS. 2-4, the both-ends-supported beam structure is formed on the cavity C formed in the substrate 1. Thus, by forming the beam structure, a heat capacity of the sensor portion can be reduced, and heat conduction can be reduced. As a result, power consumption at the time of the heating can be reduced.

Second Embodiment

Figure 13:
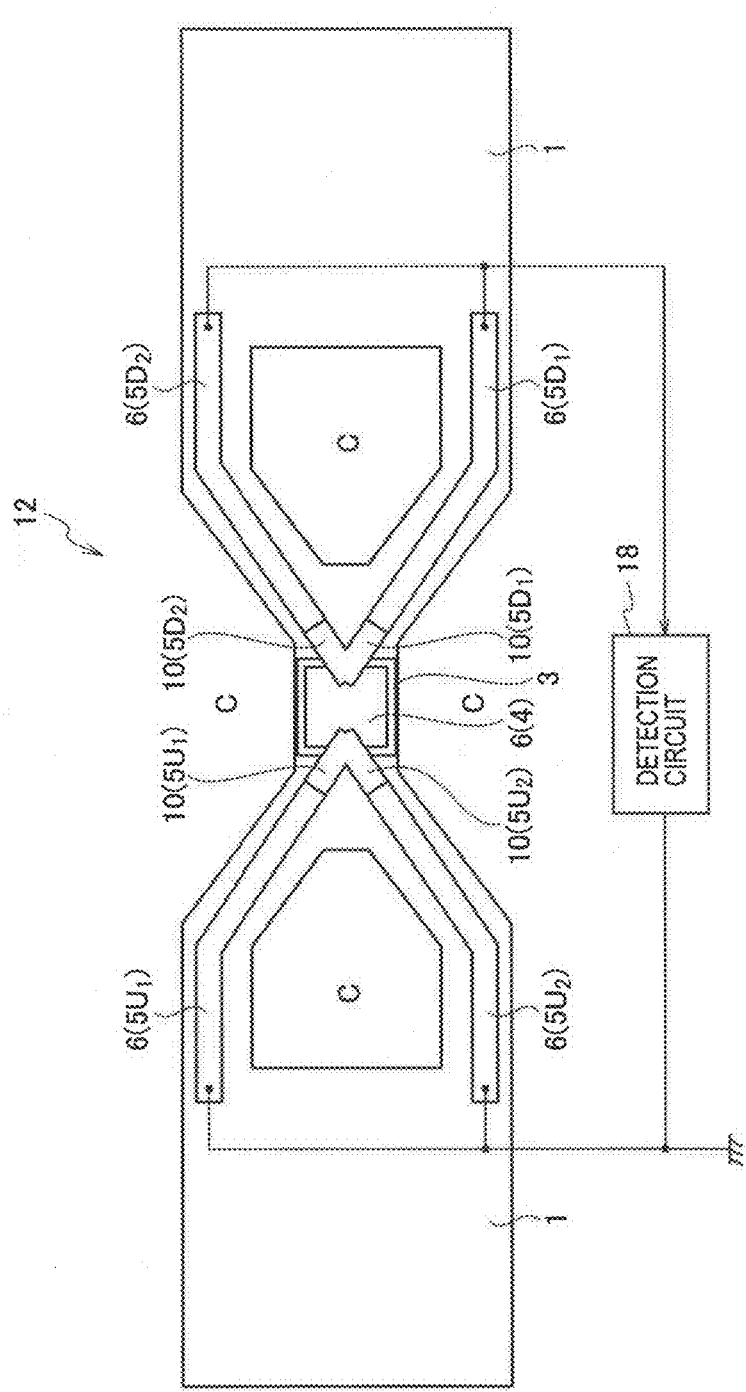
FIG. 13 is a schematic planar pattern configuration diagram showing a limiting-current type gas sensor according to a second embodiment.
Figure 14:
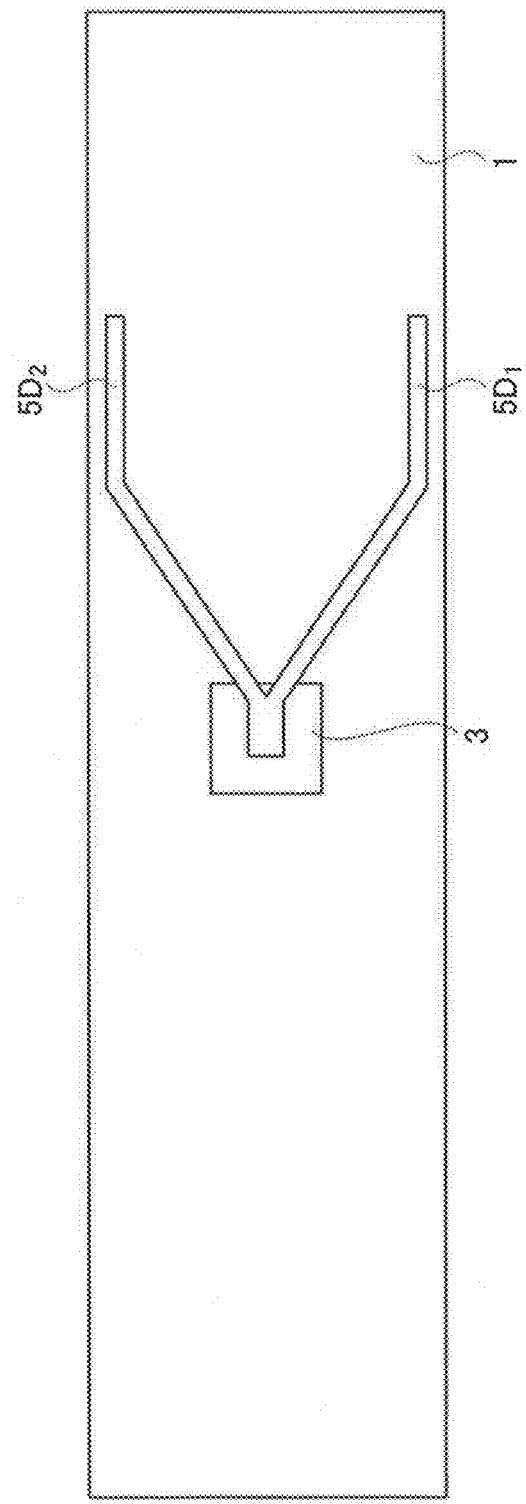
FIG. 14 is a schematic plan view showing a process of a fabrication method of the limiting-current type gas sensor according to the second embodiment (Phase 1).
Figure 15:
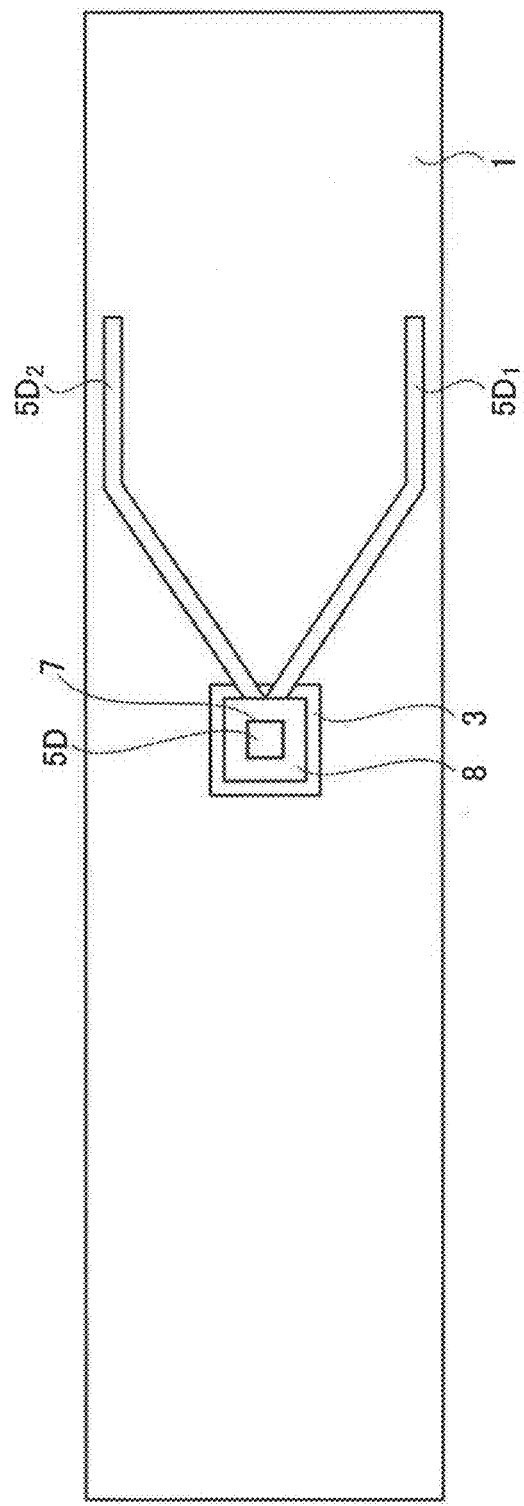
FIG. 15 is a schematic plan view showing a process of the fabrication method of the limiting-current type gas sensor according to the second embodiment.
Figure 16:
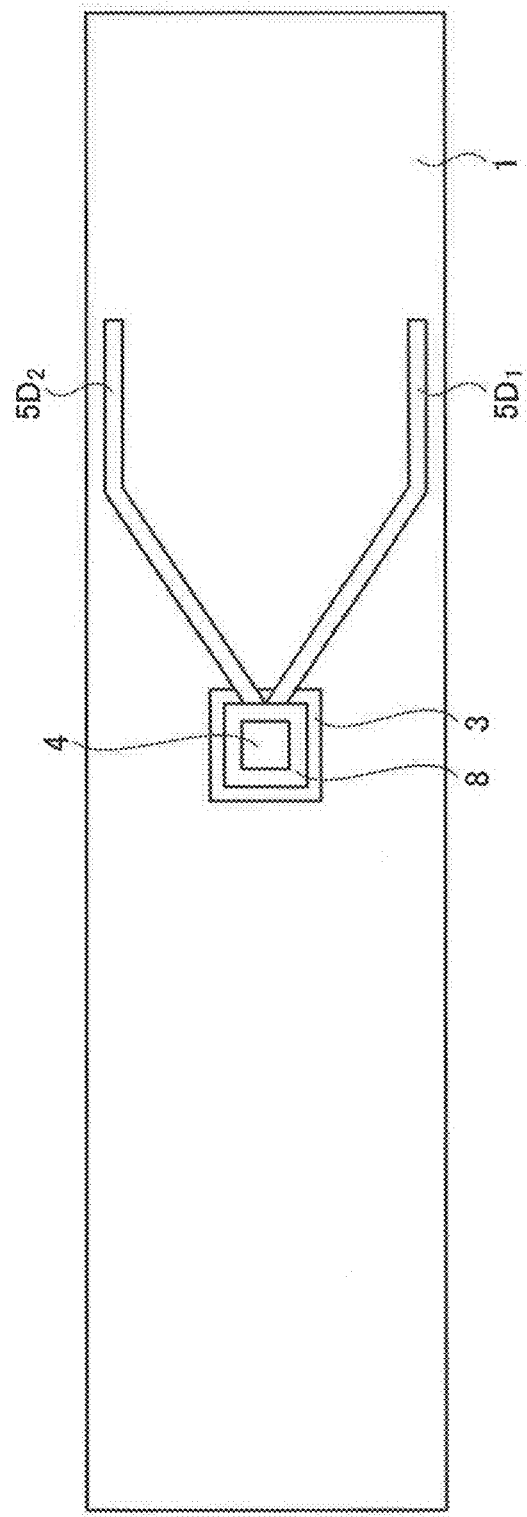
FIG. 16 is a schematic plan view showing a process of the fabrication method of the limiting-current type gas sensor according to the second embodiment (Phase 3).

FIG. 13 shows a schematic planar pattern configuration of a limiting-current type gas sensor according to a second embodiment. As shown in FIG. 2, in the first embodiment, the porous lower electrode 5D and the porous lower electrode 5U respectively are disposed only on one arm of two arms at each side among four arms of the both-ends-supported beam structure (straddle-mounted beam structure). On the other hand, as shown in FIG. 13, in the second embodiment, porous lower electrodes $5D_1$, $5D_2$, and porous upper electrodes $5U_1$, $5U_2$ respectively are disposed on both arms of two arms at each side among four arms of the both-ends-supported beam structure (straddle-mounted beam structure). Moreover, the porous lower electrodes $5D_1$, $5D_2$ are electrically connected to each other. Similarly, the porous upper electrodes $5U_1$, $5U_2$ are also electrically connected to each other.

As shown in FIG. 13, the limiting-current type gas sensor 12 according to the second embodiment includes: a substrate 1; porous lower electrodes $5D_1$, $5D_2$ disposed on the substrate 1; an insulating film 8 disposed on the porous lower electrodes $5D_1$, $5D_2$; a solid electrolyte layer 4 disposed on the porous lower electrodes $5D_1$, $5D_2$ in an opening 7 formed by patterning the insulating film 8, and further disposed on the insulating film 8 surrounding the opening 7; and porous upper electrodes $5U_1$, $5U_2$ disposed on the solid electrolyte layer 4 so as to be opposite to the porous lower electrode 5D, and so as to be disposed in a substantially vertical direction with respect to the substrate 1.

In this case, the insulating film 8 realizes non-contact between the edge face of the solid electrolyte layer 4 and the porous lower electrodes $5D_1$, $5D_2$, in order to suppress the intake of oxygen (O) ion from the edge face of the solid electrolyte layer 4, and thereby the surface-conduction current component between the porous upper electrodes $5U_1$, $5U_2$ and the porous lower electrodes $5D_1$, $5D_2$ can be reduced.

Moreover, as shown in FIG. 13, the limiting-current type gas sensor 12 according to the second embodiment includes a detection circuit 18 configured to detect a predetermined gas density in measured gas with a limiting current method by applying voltage between the porous upper electrodes $5U_1$, $5U_2$ and the porous lower electrodes $5D_1$, $5D_2$. In the present embodiment, the detection circuit 18 can detect the oxygen density on the basis of a limiting current. Moreover, the detection circuit 18 can detect vapor density on the basis of the limiting current.

Moreover, as shown in FIG. 13, the limiting-current type gas sensor 12 according to the second embodiment may include: first low-thermal expansion films $6(5U_1)$, $6(5U_2)$ for stress relaxation respectively disposed on the porous upper electrodes $5U_1$, $5U_2$; second low-thermal expansion films 6 $(5D_1)$, 6 $(5D_2)$ for stress relaxation disposed on the porous lower electrodes $5D_1$, $5D_2$; and a third low-thermal expansion film 6(4) for stress relaxation disposed on the solid electrolyte layer 4.

Moreover, as shown in FIG. 13, the limiting-current type gas sensor 12 according to the second embodiment may include: first porous insulating films 10 $(5U_1)$, 10 $(5U_2)$ for suppressing warpage disposed on the porous upper electrodes $5U_1$, $5U_2$ so as to extend over between the first low-thermal expansion films 6 $(5U_1)$, 6 $(5U_2)$ for stress relaxation and the third low-thermal expansion film 6(4) for stress relaxation in a planar view; and second porous insulating films 10 $(5D_1)$, 10 $(5D_2)$ for suppressing warpage disposed on the porous lower electrodes $5D_1$, $5D_2$ so as to extend over between the second low-thermal expansion films 6 $(5D_1)$, 6 $(5D_2)$ for stress relaxation and the third low-thermal expansion film 6(4) for stress relaxation in a planar view.

Moreover, the limiting-current type gas sensor 12 may include a gas intake film 3 disposed on the substrate 1, the porous lower electrodes $5D_1$, $5D_2$ may be disposed on the gas intake film 3. Other configurations are the same as those of the first embodiment.

(Fabrication Method)

Figure 17:
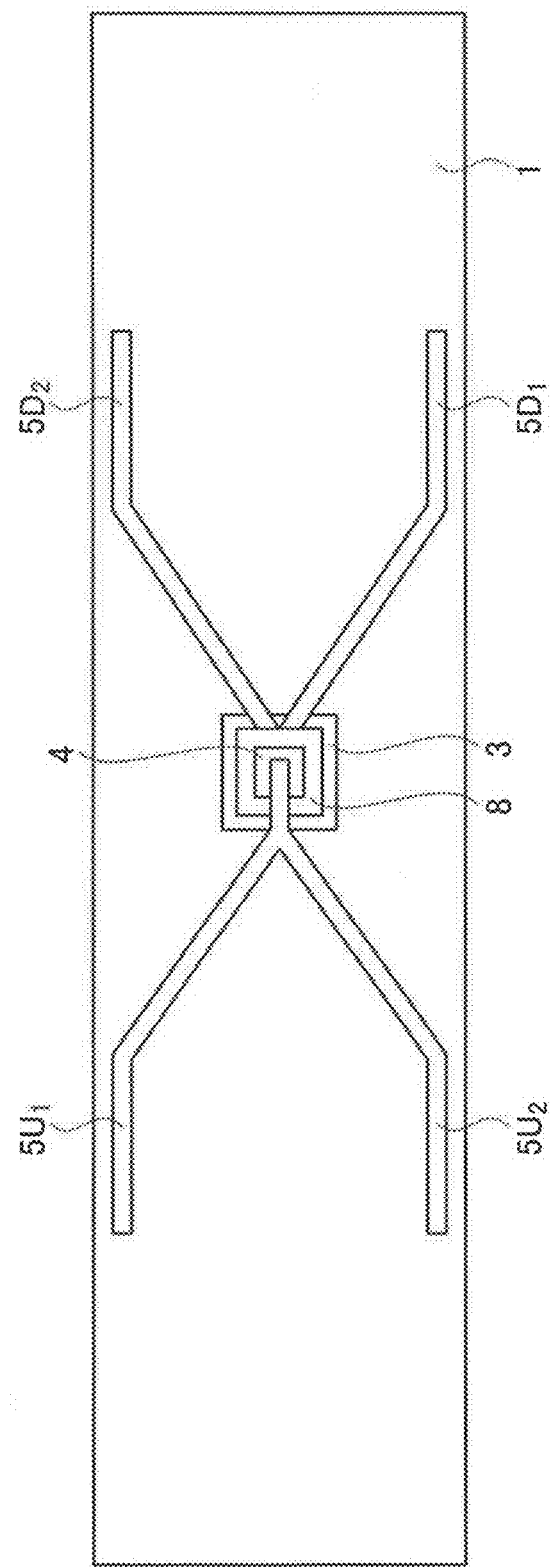
FIG. 17 is a schematic plan view showing a process of the fabrication method of the limiting-current type gas sensor according to the second embodiment (Phase 4).

As shown in FIGS. 14-17, a fabrication method of the limiting-current type gas sensor according to the second embodiment includes: forming porous lower electrodes $5D_1$, $5D_2$ on a substrate 1 (FIG. 14); forming an insulating film 8 on the porous lower electrodes $5D_1$, $5D_2$; patterning the insulating film 8 in order to form an opening 7 (FIG. 15); forming a solid electrolyte layer 4 on the porous lower electrodes $5D_1$, $5D_2$ in the opening 7 and on the insulating film 8 surrounding the opening 7 (FIG. 16); and forming porous upper electrodes $5U_1$, $5U_2$ on the solid electrolyte layer 4 so as to be opposite to the porous lower electrodes $5D_1$, $5D_2$, and so as to be disposed in a substantially vertical direction with respect to the substrate 1 (FIG. 17). In this case, the insulating film 8 realizes non-contact between the edge face of the solid electrolyte layer 4 and the porous lower electrodes $5D_1$, $5D_2$, in order to suppress the intake of oxygen (O) ion from the edge face of the solid electrolyte layer 4, and thereby the surface-conduction current component between the porous upper electrodes $5U_1$, $5U_2$ and the porous lower electrodes $5D_1$, $5D_2$ can be reduced.

Figure 18:
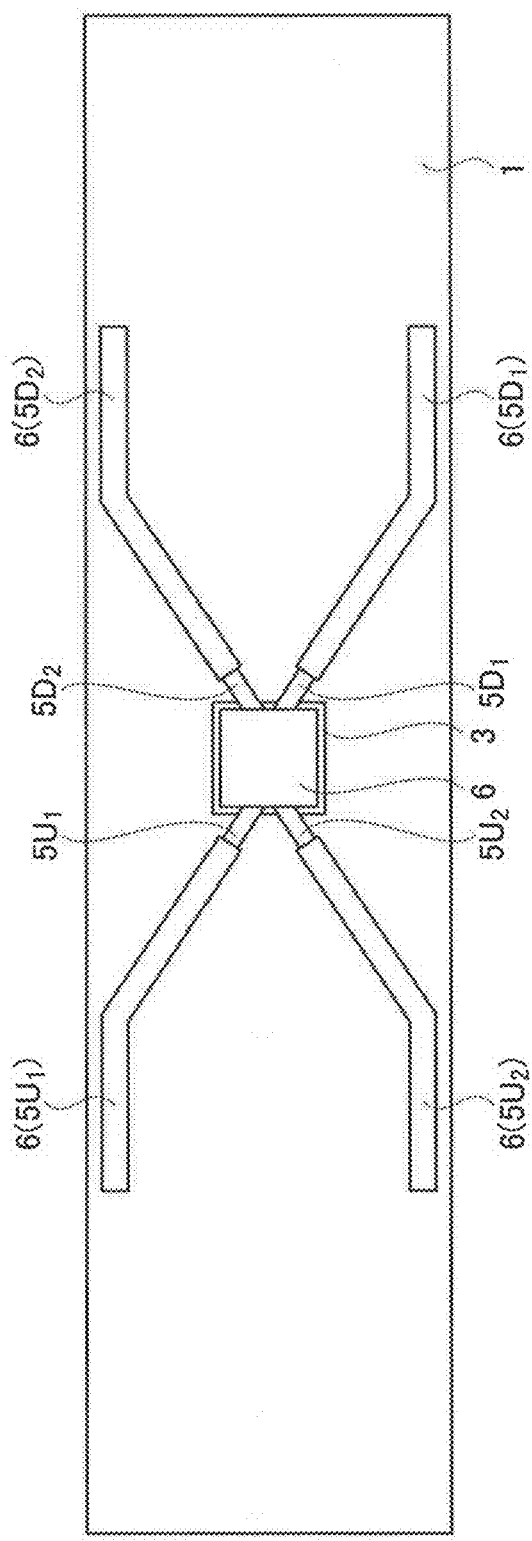
FIG. 18 is a schematic plan view showing a process of the fabrication method of the limiting-current type gas sensor according to the second embodiment (Phase 5).

Moreover, as shown in FIG. 18, the fabrication method of the limiting-current type gas sensor according to the second embodiment further includes forming first low-thermal expansion films $6(5U_1)$, $6(5U_2)$ for stress relaxation on the porous upper electrodes $5U_1$, $5U_2$, forming second low-thermal expansion films $6(5D_1)$, $6(5D_2)$ for stress relaxation on the porous lower electrodes $5D_1$, $5D_2$, and forming a third low-thermal expansion film 6(4) for stress relaxation on the solid electrolyte layer 4.

Figure 19:
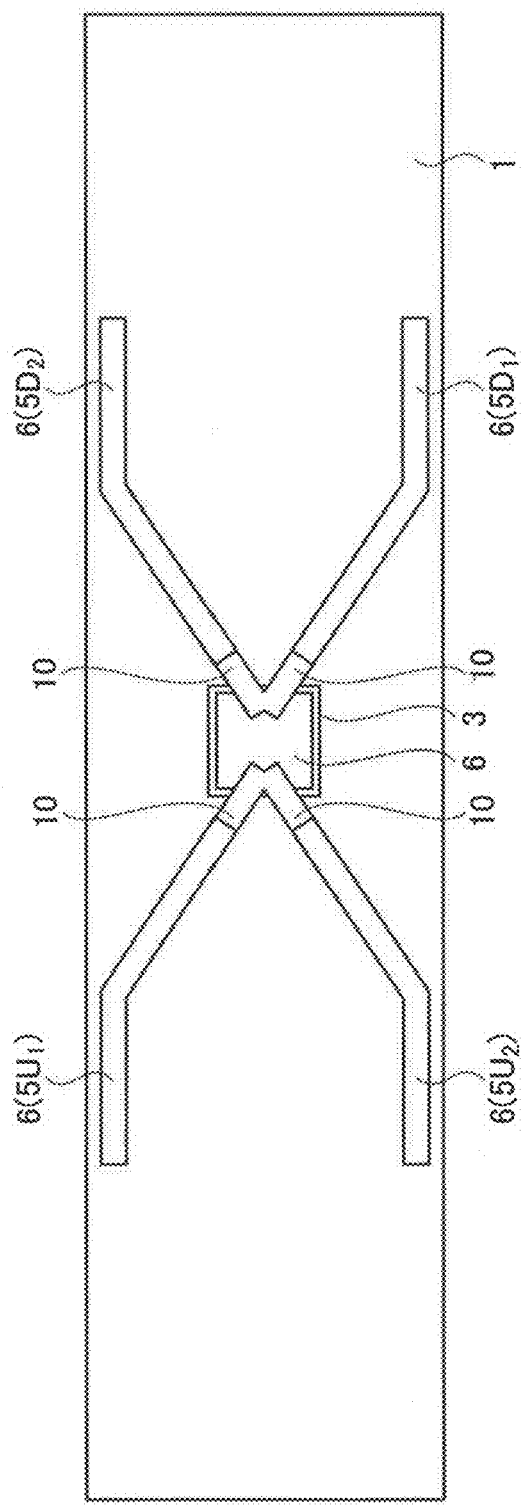
FIG. 19 is a schematic plan view showing a process of the fabrication method of the limiting-current type gas sensor according to the second embodiment (Phase 6).

As shown in FIG. 19, the fabrication method of the limiting-current type gas sensor according to the second embodiment further includes: forming first porous insulating films $10(5U_1)$, $10(5U_2)$ for suppressing warpage on the porous upper electrodes $5U_1$, $5U_2$ so as to extend over between the first low-thermal expansion films $6(5U_1)$, $6(5U_2)$ for stress relaxation and the third low-thermal expansion film $6(4)$ for stress relaxation in a planar view; and forming second porous insulating films $10(5D_1)$, $10(5D_2)$ for suppressing warpage on the porous lower electrodes $5D_1$, $5D_2$ so as to extend over between the second low-thermal expansion films $6$ $(5D_1)$, $6$ $(5D_2)$ for stress relaxation and the third low-thermal expansion film $6(4)$ for stress relaxation in a planar view.

Moreover, as shown in FIG. 13, the fabrication method of the limiting-current type gas sensor according to the second embodiment further includes forming both-ends-supported beam structure on a cavity formed in the substrate 1 by etching the substrate 1.

Moreover, as shown in FIG. 13, the fabrication method of the limiting-current type gas sensor according to the second embodiment may include forming a gas intake film 3 on the substrate 1, and may form the porous lower electrodes $5D_1$, $5D_2$ on the gas intake film 3.

Since only the structure of disposing the porous lower electrodes $5D_1$, $5D_2$ and the porous upper electrodes $5U_1$, $5U_2$ on both arms of two arms at each side is different from that of the first embodiment, other detailed fabricating processes for respective units are the same as those of the first embodiment.

Hereinafter, in explanations common to the first and second embodiments, the first and second embodiments will be merely described as the embodiments.

(Beam Structure)

Figure 20A:
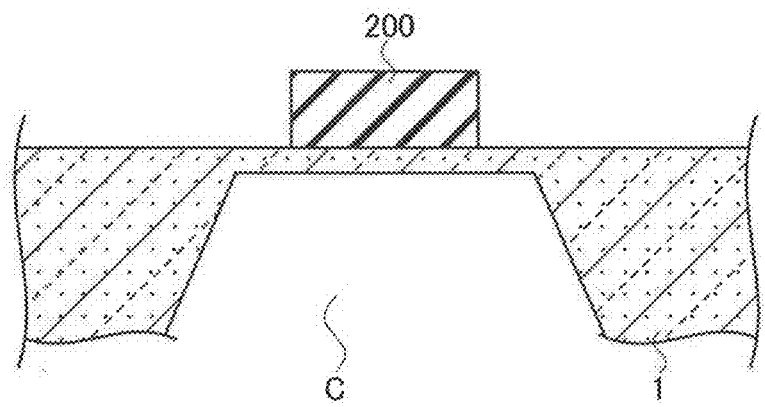
FIG. 20A is a schematic cross-sectional structure diagram showing a process (formation process of beam structure) of the fabrication method of the limiting-current type gas sensor according to the embodiments.
Figure 20B:
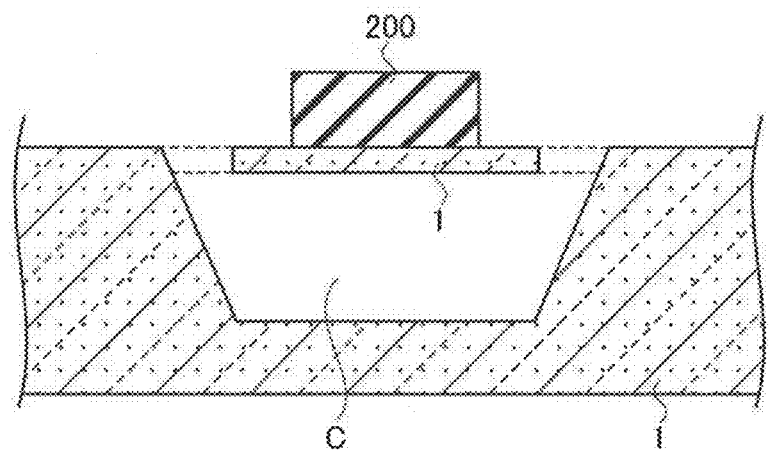
FIG. 20B is a schematic cross-sectional structure diagram showing a process (another formation process of beam structure) of the fabrication method of the limiting-current type gas sensor according to the embodiments.

FIG. 20A shows a schematic cross-sectional structure showing a process (formation process of beam structure) of the fabrication method of the limiting-current type gas sensor according to the embodiments. FIG. 20B shows a process (another formation process of beam structure) of the fabrication method of the limiting-current type gas sensor according to the embodiments.

As the beam structure having MEMS structure, it is possible to adopt an open type structure of forming a cavity area C in a bottom of the substrate 1 as an open structure, as shown in FIG. 20A, or a ship type structure of forming a cavity area C in an inside of the substrate 1, as shown in FIG. 20B. Anisotropic etching of the silicon substrate, etc. can be applied to both structures. In each of FIGS. 20A and 20B, a micro heater 2 is formed in the thin-layered substrate 1 portion, but illustration thereof is omitted. Moreover, the vertical sensor structure of the limiting-current type gas sensor according to the embodiments is expressed with a device heating unit 200.

Figure 21A:
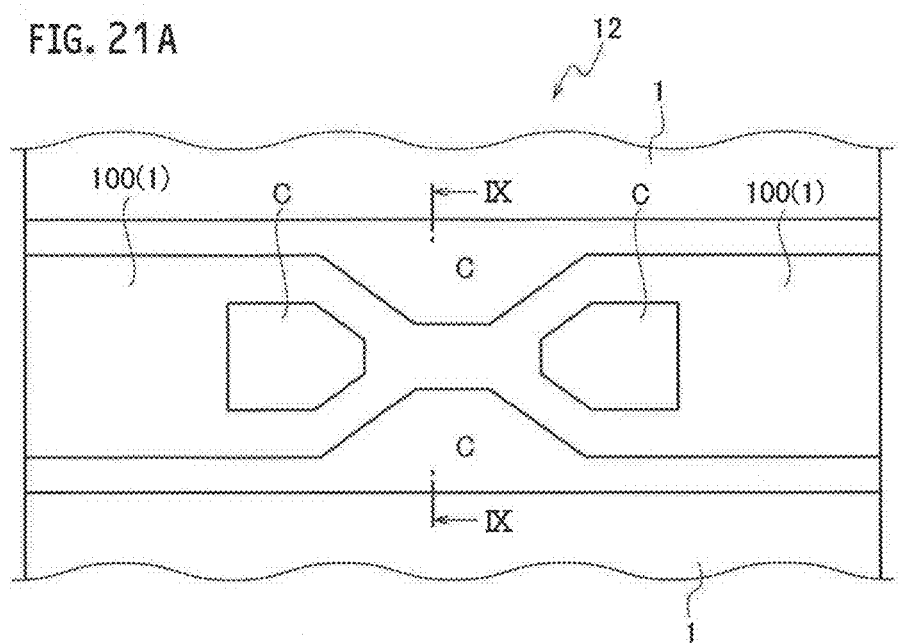
FIG. 21A is a layout chart (top view diagram) showing the beam structure of the limiting-current type gas sensor according to the embodiments.
Figure 21B:
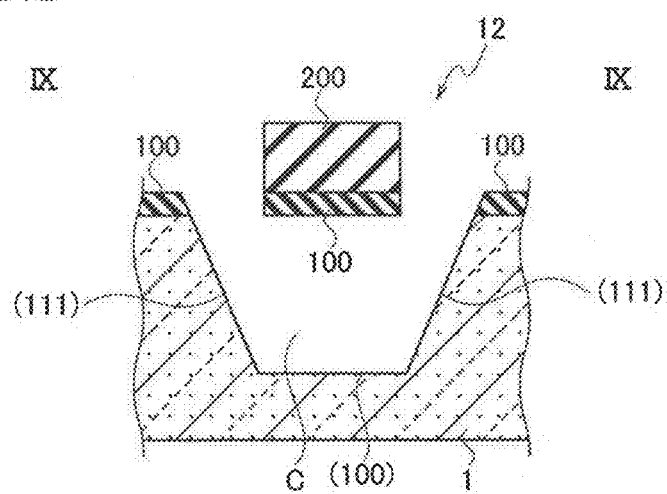
FIG. 21B is a schematic cross-sectional structure diagram taken in the line IX-IX of FIG. 21A.

FIG. 21A shows a layout chart (top view diagram) of the beam structure of the limiting-current type gas sensor according to the embodiments, and FIG. 21B shows a schematic cross-sectional structure taken in the IX-IX of FIG. 21A.

In FIG. 21, a silicon substrate having a plane (100) is used as the substrate 1, and a cavity C of which a bottom surface is the plane (111) and a side surface is a plane (100) is formed by anisotropic etching at a bottom of the device heating unit 200.

A laminated film 100 including a silicon oxide film/silicon nitride film including the micro heater formed containing polysilicon is formed on the surface of the silicon substrate 1. An area of the device heating unit 200 is approximately 0.1 mm$^2$, for example.

In the structure example shown in FIGS. 21A and 21B, the laminated film 100 including the micro heater is formed at the bottom of the device heating unit 200 having vertical sensor structure, and the substrate 1 is removed therefrom. More specifically, in the first and second embodiments, the thin-layered substrate 1 is removed therefrom, and only the laminated film 100 including the micro heater may be formed.

The micro heater 2 in the limiting-current type gas sensor according to the embodiments can be formed by the following process flow.

Firstly, a 3 um-Phosphorus Silicon Glass (PSG) film is formed on the Si substrate 1, SiN is formed thereon, and then SiN patterning is performed (SiN is removed from a heavily doping portion). Next, polysilicon is formed, for example, phosphorus P is diffused to the polysilicon by an annealing process at approximately 1000 degrees C. to make highly-doped polysilicon. A portion with SiN is made into lowly-doped polysilicon. Furthermore, a vertical sensor structure is formed, and PSG etching is performed with BHF (5:1) to from the beam structure.

As mentioned above, according to the embodiments, the micro heater 2 having the beam structure can be easily formed on the cavity C.

In the limiting-current type gas sensor according to the embodiments, the micro heater 2 is disposed in the laminated film 100 portion shown in FIGS. 21A and 21B. The micro heater 2 may be formed by the following process flow.

Firstly, the laminated film 100 which is a multilayered insulating film including $SiO_2/SiN/SiO_2$ is formed on the Si (100) substrate 1, and then a Pt heater (micro heater 2) is formed thereon. Next, the device heating unit 200 is formed on the micro heater 2. Furthermore, the cavity C is formed with performing anisotropic etching of Si substrate 1 using TMAH solution.

As mentioned above, according to the embodiments, the micro heater 2 having the beam structure can be easily formed on the cavity C.

(Operational Principle)

Operation for Detecting Gas Density

The principle of the limiting-current type gas sensor is as follows: Firstly, if a zirconia solid electrolyte is heated at hundreds of degrees C. and voltage is applied to the zirconia solid electrolyte, an oxygen ion ionized with a catalyst electrode will conduct from one side of solid electrolyte to another side thereof. If an amount of oxygen gas inhaled to the electrolyte using small holes, porousness, etc. is limited at that time, saturation phenomena in which a current becomes constant value will appear even if the voltage is increased. Such a current is called a limiting current and is proportional to a surrounding oxygen density. Accordingly, if a constant voltage is applied thereto, the oxygen density can be detected on the basis of a flowing current value. It is also possible to detect a vapor density in accordance with the similar principle if the voltage to be applied is switched.

Figure 22:
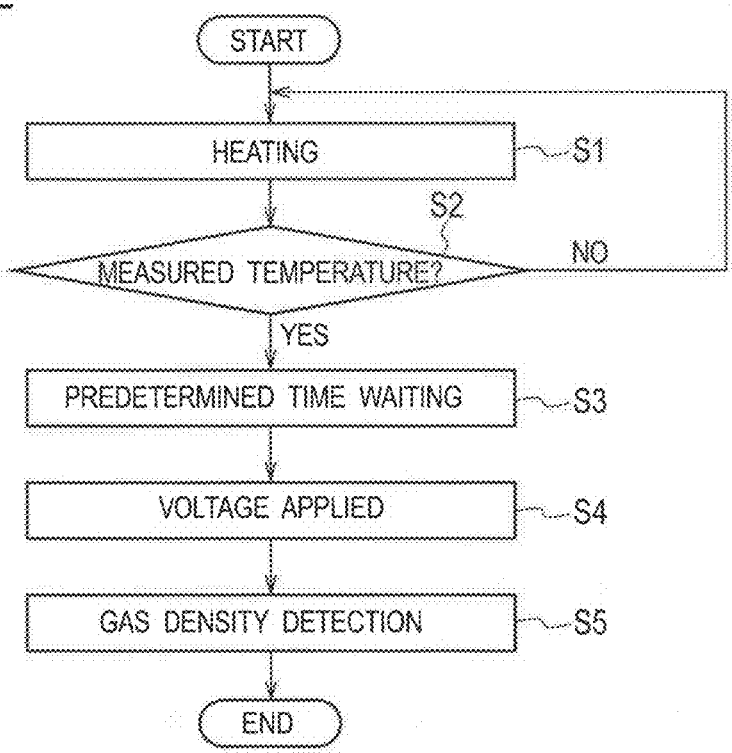
FIG. 22 is a flow chart showing an operation for detecting a gas density using the limiting-current type gas sensor according to the embodiments.
Figure 23:
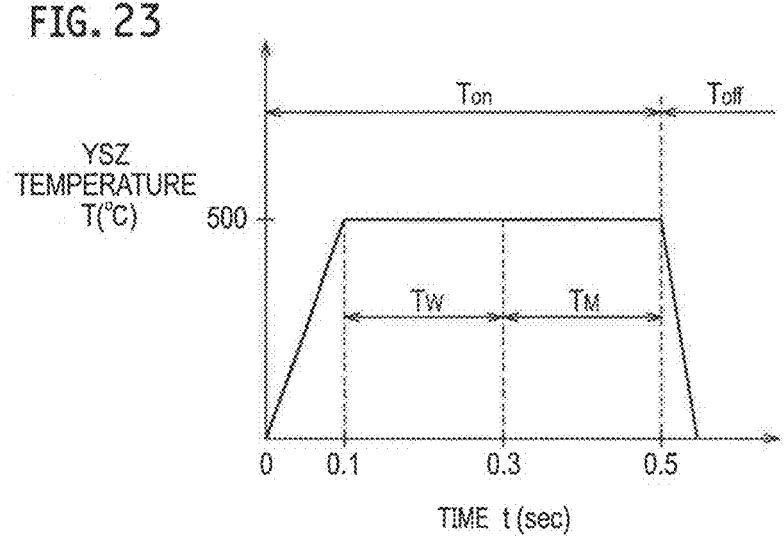
FIG. 23 is a schematic diagram showing a relationship between a YSZ temperature and time in the gas density detecting operation, in the limiting-current type gas sensor according to the embodiments.

FIG. 22 shows a flow chart showing an operation for detecting a gas density using the limiting-current type gas sensor according to the embodiments. Moreover, FIG. 23 schematically shows, a relationship between a YSZ temperature and time in the gas density detecting operation, in the limiting-current type gas sensor according to the embodiments, and FIG. 24 shows a schematic cross-sectional structure for explaining an operational principle.

Figure 24:
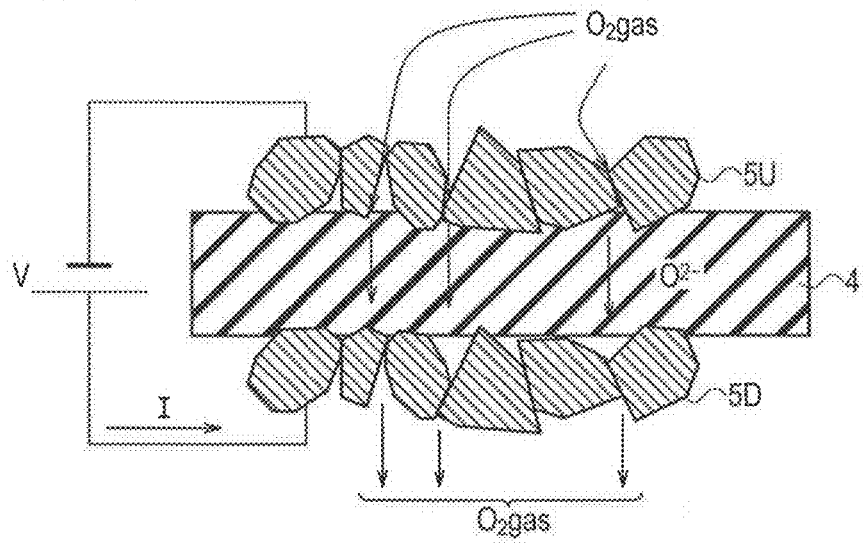
FIG. 24 is a schematic cross-sectional structure diagram for explaining an operational principle of the limiting-current type gas sensor according to the embodiments.

If the solid electrolyte layer 4 is heated up to approximately hundreds of degrees C., e.g., 500 degrees C., by the micro heater 2, and voltage is applied between the porous upper electrode (cathode) 5U and the porous lower electrode (anode) 5D to flow an electric current I thereinto, oxygen ion is injected into the solid electrolyte layer 4 by an electrochemical reaction with $O^2+4e^-\leftrightarrow 2O^{2-}$, in the porous upper electrode (cathode) 5U, as shown in FIG. 24. On the other hand, oxygen gas is released by a reaction of $2O^{2-}\leftrightarrow O^2+4e^-$, in the porous lower electrode (anode) 5D.

Figure 25:
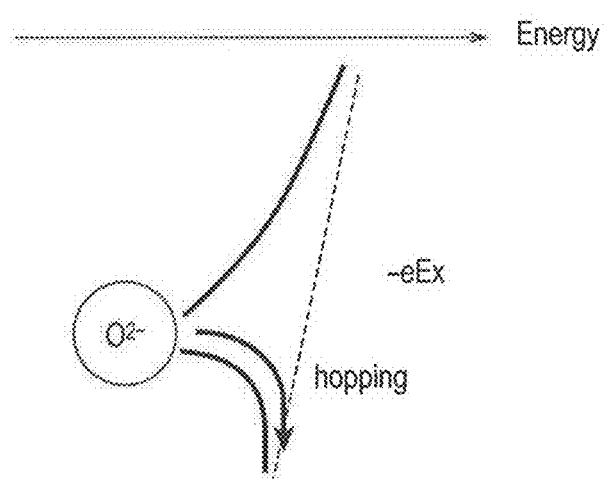
FIG. 25 is an energy diagram for explaining a hopping conduction of oxygen ion ($O^2$), in the limiting-current type gas sensor according to the embodiments.

In the solid electrolyte layer 4, the oxygen ion ($O^{2-}$) is propagated on the basis of hopping conduction. FIG. 25 schematically shows an energy diagram for explaining the hopping conduction of oxygen ion ($O^{2-}$). If an electric field EX is applied to the solid electrolyte layer 4, a bottom of the conductor will be inclined at an angle of only $-eE_X$, due to the effect. The hopping conduction of oxygen ion ($O^{2-}$) is performed with thermal excitation since a conduction barrier height of the oxygen ion ($O^{2-}$) is reduced only for the amount thereof.

Figure 26:
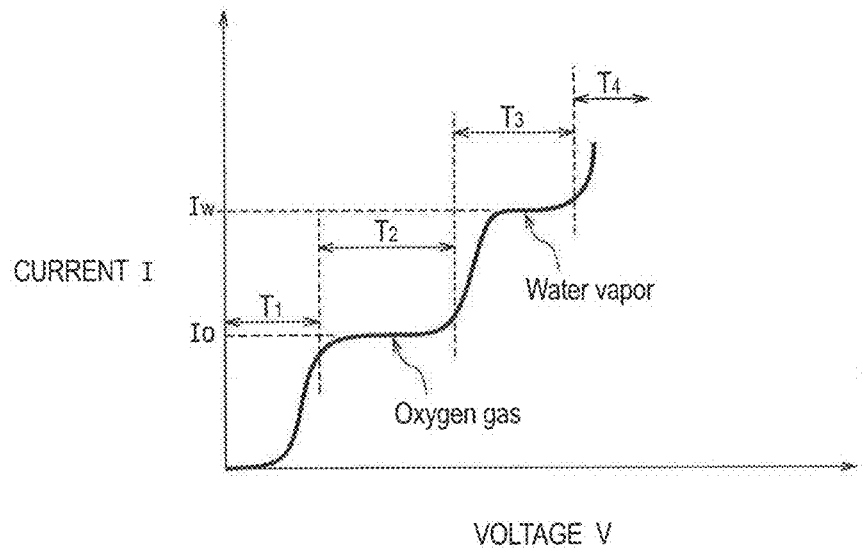
FIG. 26 is a schematic explanatory diagram of current-voltage characteristics, in the limiting-current type gas sensor according to the embodiments.

If an amount of oxygen gas inhaled to the electrolyte 4 is limited, saturation phenomena in which a current becomes constant value will appear even if the voltage is increased. FIG. 26 schematically shows a limiting current in current-voltage characteristics, in the limiting-current type gas sensor according to the embodiments. More specifically, in FIG. 26, an electric current which appears at a period $T_2$ expresses a limiting current $I_O$ with respect to the oxygen gas, and an electric current which appears at a period $T_3$ expresses a limiting current $I_W$ with respect to vapor. Since the limiting currents $I_O$, $I_W$ are proportional to surrounding oxygen density and vaper density, values of the limiting currents $I_O$, $I_W$ are previously associated with values of the oxygen density and vaper density to be registered into the detection circuit 8. Thus, the oxygen density and vaper density respectively corresponding to the values of the limiting currents $I_O$, $I_W$ can be detected by measuring the values of the limiting currents $I_O$, $I_W$. Moreover, if the voltage V applied between porous upper electrode (cathode) 5U and the porous lower electrode 5D, it is possible to detect not only the oxygen density but also the vapor density.

An operation for detecting the gas density using the limiting-current type gas sensor 12 according to the embodiments will now be explained with reference to FIGS. 22 and 23. In FIG. 23, $T_{on}$ corresponds to a heater ON period, and $T_{off}$ corresponds to a heater OFF period. A heating power input during the heater ON period $T_{on}$ is approximately 5 mW, for example.

(a) Firstly, the sensor is heated up to measured temperature (e.g., 500 degrees C.) from a room temperature using the micro heater 2 (Step S1→S2: NO→S1→ . . . , in FIG. 22). As shown in FIG. 23, YSZ temperature T rises from 0 degrees C. to approximately 500 degrees C. during time t=0 to t=0.1 second.

(b) If the temperature of the sensor reaches the measured temperature (Step S2: YES, in FIG. 22), wait for predetermined time until it is stabilized. As shown in FIG. 23, the YSZ temperature T is held at approximately 500 degrees C. during the waiting period $T_W$ of time t=0.1 second to t=0.3 second.

(c) Next, the voltage is applied between the porous upper electrode 5U and the porous lower electrode 5D (Step S3→S4, in FIG. 22). As shown in FIG. 23, the YSZ temperature T is held at approximately 500 degrees C. during the measurement period $T_M$ of time t=0.3 second to t=0.5 second.

(d) Next, the gas density corresponding to the limiting current is detected by measuring the value of the limiting current (Step S5).

(e) Next, the micro heater 2 is turned OFF, and the sensor is cooled down. As shown in FIG. 23, the YSZ temperature T is cooled from approximately 500 degrees C. to the room temperature, after time t=0.5 second.

In the temperature cycle explained above, the heating, the waiting, the measuring, and the cooling may be repeated in one cycle during approximately one minute, for example.

(Electrochemical Reaction)

Figure 27:
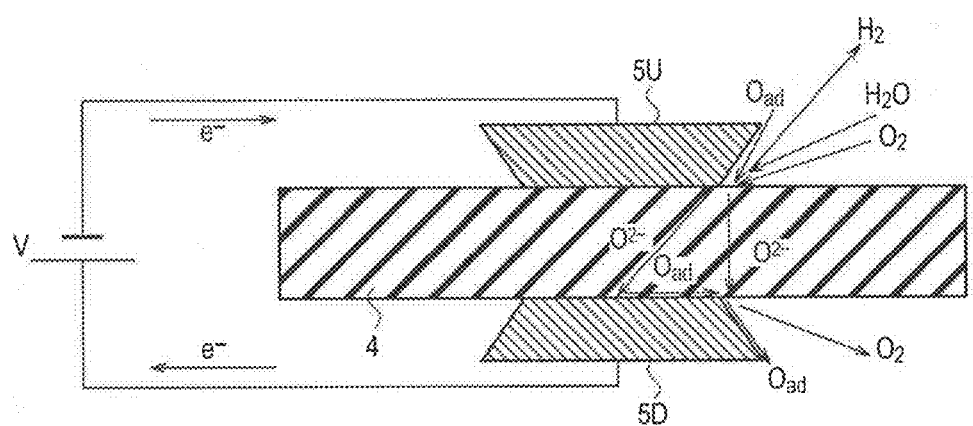
FIG. 27 is a schematic cross-sectional diagram for explaining the ionic conduction, in the limiting-current type gas sensor according to the embodiments.

FIG. 27 shows a schematic cross-sectional structure for explaining the ionic conduction, in the limiting-current type gas sensor according to the embodiments.

With reference to FIGS. 26 and 27, the electrochemical reaction in the limiting-current type gas sensor according to the embodiments will now be explained.

(a) If YSZ4 is heated up to about 500 degrees C., for example, by the micro heater 2, the voltage V is applied between the cathode 5U and the anode 5D to flow the electric current I thereinto, the electric current is increased shown in FIG. 26 and then reaches the limiting current value $I_O$, during the period $T_1$. During the period $T_1$ shown in FIG. 26, the oxygen ion $O^{2-}$ is diffused in YSZ4 due to an electrochemical reaction of $O^2+4e^-\leftrightarrow 2O^{2-}$. At this time, the flow rate of the oxygen gas $O_2$ is larger than a diffusion rate of the oxygen ion $O^{2-}$.

(b) In the period $T_2$ shown in FIG. 26 where the limiting current value $I_O$ is held, the electrolysis reaction of the oxygen gas molecules occurs, and then the oxygen ion $O^{2-}$ is injected into the YSZ4 due to the electrochemical reaction of $O^2+4e^-\leftrightarrow 2O^{2-}$, at the interface between the cathode 5U and the YSZ4, as shown in FIG. 27. On the other hand, at the interface between the anode 5D and the YSZ4, the oxygen gas $O_2$ is released due to the reaction of $2O^{2-}\leftrightarrow O^2+4e^-$.

(c) If the temperature T of YSZ4 is held at approximately 500 degrees C., for example, and the voltage V is further increased, the electric current I is increased and then is reached the limiting current $I_W$ at the period $T_3$ shown in FIG. 26.

(d) During the period $T_3$ shown in FIG. 26 where the limiting current $I_W$ is held, the electrolysis reaction of adsorbed oxygen gas $O_{ad}$ and the electrolysis reaction of vapor ($H_2O$) occur. As shown in FIG. 27, at the interface between the cathode 5U and the YSZ4, the oxygen ion $O^{2-}$ is injected into the YSZ4 due to the electrochemical reaction of $O^2+4e^-\leftrightarrow 2O^{2-}$. Moreover, the hydrogen is released due to the electrochemical reaction of $H_2O+2e^-\leftrightarrow H_2+O^{2-}$. More specifically, the vapor ($H_2O$) is electrolyzed, and the oxygen ion $O^2$ is moved by hopping conduction in the inside of the solid electrolyte layer 4. On the other hand, at the interface between the anode 5D and the YSZ4, the oxygen gas $O_2$ is released due to the reaction of $2O^{2-}\leftrightarrow O_2+4e^-$, by electrolysis of the adsorbed oxygen gas $O_{ad}$. Similarly, the oxygen gas $O_2$ is released due to the reaction of $2O^{2-}\leftrightarrow O_2+4e^-$, by electrolysis of the vapor ($H_2O$).

(e) If the temperature T of YSZ4 is held at approximately 500 degrees C., for example, and the voltage V is further increased, the electric current I is increased, and the electrolysis reaction of adsorbed oxygen gas $O_{ad}$ and the electrolysis reaction of vapor ($H_2O$) occur, during the period $T_4$ shown in FIG. 26. Furthermore, electrolysis of the YSZ4 occurs. As shown in FIG. 27, at the interface between the cathode 5U and the YSZ4, the oxygen ion $O^2$ is injected into the YSZ4 due to the electrochemical reaction of $O_2+4e^-\leftrightarrow 2O^{2-}$. Moreover, the hydrogen is released due to the electrochemical reaction of $H_2O+2e^-\leftrightarrow H_2+O^{2-}$. More specifically, the vapor ($H_2O$) is electrolyzed, and the oxygen ion $O^{2-}$ is moved by hopping conduction in the inside of the solid electrolyte layer 4.

On the other hand, at the interface between the anode 5D and the YSZ4, the oxygen gas $O_2$ is released due to the reaction of $2O^{2-} \leftrightarrow O_2 + 4e^-$, by electrolysis of the adsorbed oxygen gas $O_{ad}$. Similarly, the oxygen gas $O_2$ is released due to the reaction of $2O^{2-} \leftrightarrow O_2 + 4e^-$, by electrolysis of the vapor ($H_2O$).

Furthermore, by the electrolysis of YSZ4, the density of oxygen vacancy is dependent also on a balance with partial pressure of ambient oxygen, on the basis of the following equation $O_O^X \leftrightarrow \frac{1}{2} \cdot O_2 (g) + V_O \ldots + 2e'$. Since the electronic conductivity depends on a partial pressure of oxygen which is balanced with a solid, and the producing entropy is larger at a high temperature, and therefore the reaction is biased to the right side at the high temperature, the aforementioned equation shows that it depends also on the temperature.

(Amount of Warping: Simulation Result)

Figure 28A:
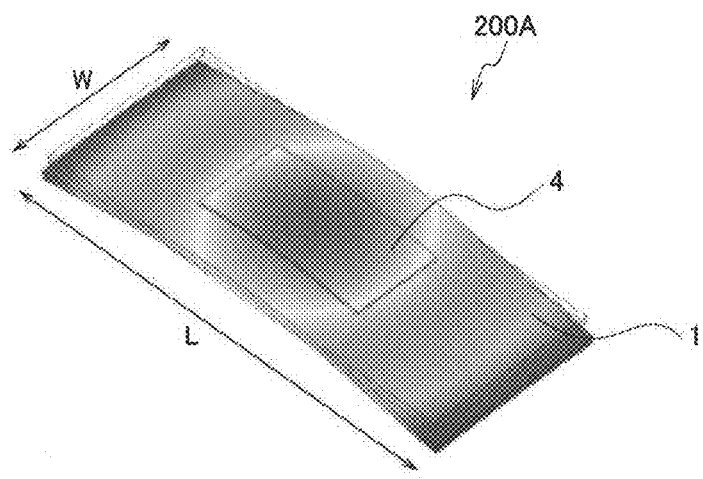
FIG. 28A is a schematic bird's-eye view showing an amount of warping at the time of heating at 500 degrees C., in a limiting-current type gas sensor according to a comparative example in which mullite is not formed on YSZ.
Figure 28B:
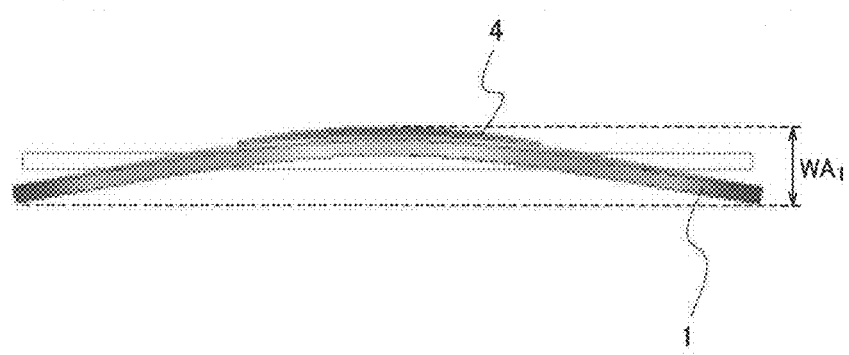
FIG. 28B is a schematic cross-sectional diagram corresponding to FIG. 28A.

In a device heating unit 200A in a limiting-current type gas sensor according to a comparative example in which mullite is not formed on the solid electrolyte layer (YSZ) 4, FIG. 28A shows a schematic bird's-eye view showing an amount of warping $WA_1$ at the time of heating at 500 degrees C., and FIG. 28B shows a schematic cross-sectional diagram corresponding to FIG. 28A. FIGS. 28A and 28B show the device heating unit 200A in the limiting-current type gas sensor according to the comparative example, and the thickness of the silicon substrate 1 having beam structure is 10 μm and the thickness of the solid electrolyte layer (YSZ) 4 is 2 μm. As the size of the device heating unit 200A, the width W is 200 μm and the length L is 500 μm.

In the device heating unit 200A in the limiting-current type gas sensor according to the comparative example in which the mullite (6, 10) is not formed on the solid electrolyte layer (YSZ) 4, a simulation result of amount of warping $WA_1$ at the time of heating at 500 degrees C. is 3.9 μm.

Figure 29A:
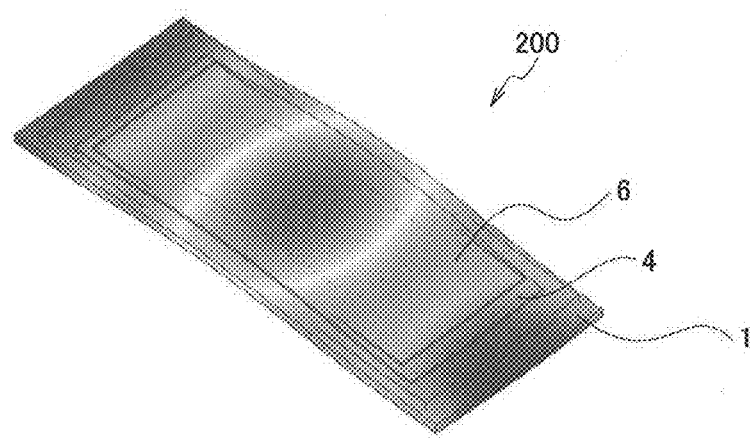
FIG. 29A is a schematic bird's-eye view showing an amount of warping at the time of heating at 500 degrees C., in the limiting-current type gas sensor according to the embodiments in which 3-μm mullite is formed on the YSZ.
Figure 29B:
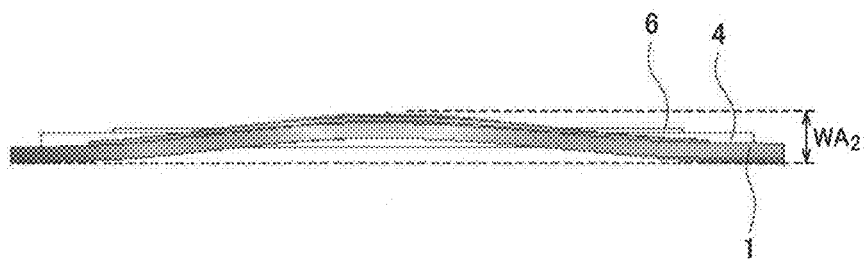
FIG. 29B is a schematic cross-sectional diagram corresponding to FIG. 29A.

In a device heating unit 200 in the limiting-current type gas sensor according to the embodiments in which 3-μm mullite is formed on the solid electrolyte layer (YSZ) 4, FIG. 29A shows a schematic bird's-eye view showing an amount of warping $WA_2$ at the time of heating at 500 degrees C., and FIG. 29B shows a schematic cross-sectional diagram corresponding to FIG. 29A. The mullite disclosed herein is a layer corresponding to the low-thermal expansion film (6, 6(5U), 6(5D)) for stress relaxation and the porous insulating film (10, 10(5U), 10(5D)) for suppressing warpage. FIGS. 29A and 29B show the device heating unit 200 in the limiting-current type gas sensor according to the embodiments, and the thickness of the silicon substrate 1 having beam structure is 10 μm and the thickness of the solid electrolyte layer (YSZ) 4 is 2 μm. As the size of the device heating unit 200, the width W is 200 μm and the length L is 500 μm.

In the device heating unit 200 in the limiting-current type gas sensor according to the embodiments in which 3-μm mullite is formed on the solid electrolyte layer (YSZ) 4, a simulation result of amount of warping $WA_2$ at the time of heating at 500 degrees C. is 1.2 μm. More specifically, the amount of the warping is reduced approximately 70%.

Figure 30A:
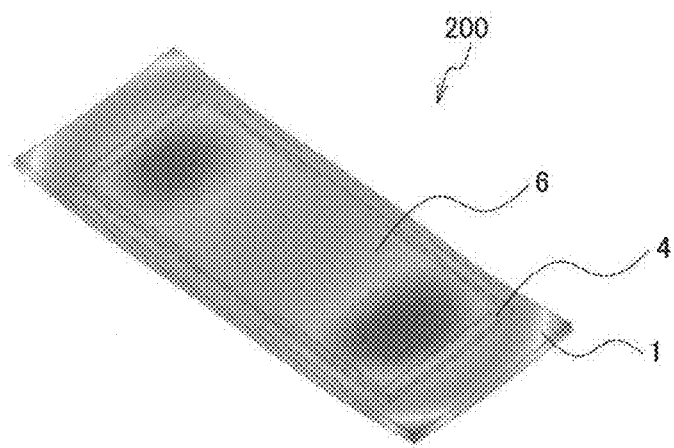
FIG. 30A is a schematic bird's-eye view showing an amount of warping at the time of heating at 500 degrees C., in the limiting-current type gas sensor according to the embodiments in which 5-μm mullite is formed on the YSZ.
Figure 30B:
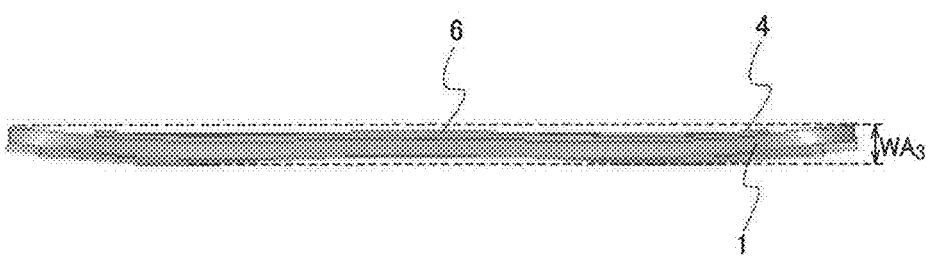
FIG. 30B is a schematic cross-sectional diagram corresponding to FIG. 30A.

In a device heating unit 200 in the limiting-current type gas sensor according to the embodiments in which 5-μm mullite is formed on the solid electrolyte layer (YSZ) 4, FIG. 30A shows a schematic bird's-eye view showing an amount of warping $WA_3$ at the time of heating at 500 degrees C., and FIG. 30B shows a schematic cross-sectional diagram corresponding to FIG. 30A. FIGS. 30A and 30B show the device heating unit 200 in the limiting-current type gas sensor according to the embodiments, and the thickness of the silicon substrate 1 having beam structure is 10 μm and the thickness of the solid electrolyte layer (YSZ) 4 is 2 μm. As the size of the device heating unit 200, the width W is 200 μm and the length L is 500 μm.

In the device heating unit 200 in the limiting-current type gas sensor according to the embodiments in which 5-μm mullite is formed on the solid electrolyte layer (YSZ) 4, a simulation result of amount of warping $WA_3$ at the time of heating at 500 degrees C. is 0.2 μm. More specifically, the amount of the warping is reduced approximately 95%.

In the above-mentioned simulation, Young's modulus of the solid electrolyte layer (YSZ) 4 is set to 210 GPa, and a coefficient of thermal expansion thereof is set to $10 \times 10^{-6}$/K. Moreover, Young's modulus of the silicon substrate 1 of beam structure is set to 185 GPa, and a coefficient of thermal expansion thereof is set to $3.35 \times 10^{-6}$/K. Young's modulus of the mullite is set to 170 GPa, and a coefficient of thermal expansion thereof is set to $2.2 \times 10^{-6}$/K. Moreover, a constituent of the mullite is $Al_2O_3$-66 mol % $SiO_2$.

From the above-mentioned simulation result, it is proved that the amount of the warping can be reduced by forming the mullite which is a layer corresponding to the low-thermal expansion film (6, 6(5U), 6(5D)) for stress relaxation and the porous insulating film (10, 10(5U), 10(5D)) for suppressing warpage.

(YSZ Annealing Temperature)

Figure 31:
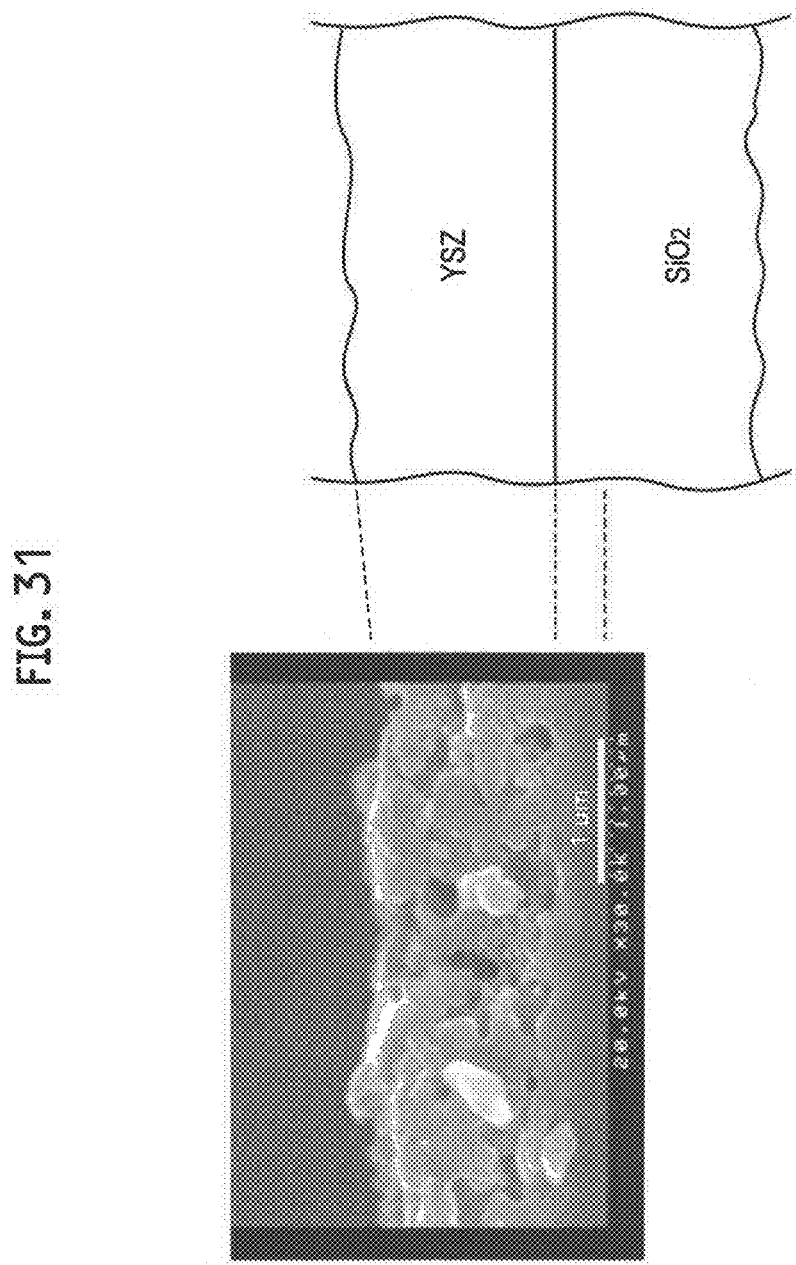
FIG. 31 shows an example of a cross-sectional Scanning Electron Microscope (SEM) photograph in a state where YSZ-10 wt % SiO$_2$ is annealed at 1200 degrees C., in the limiting-current type gas sensor according to the embodiments.
Figure 32:
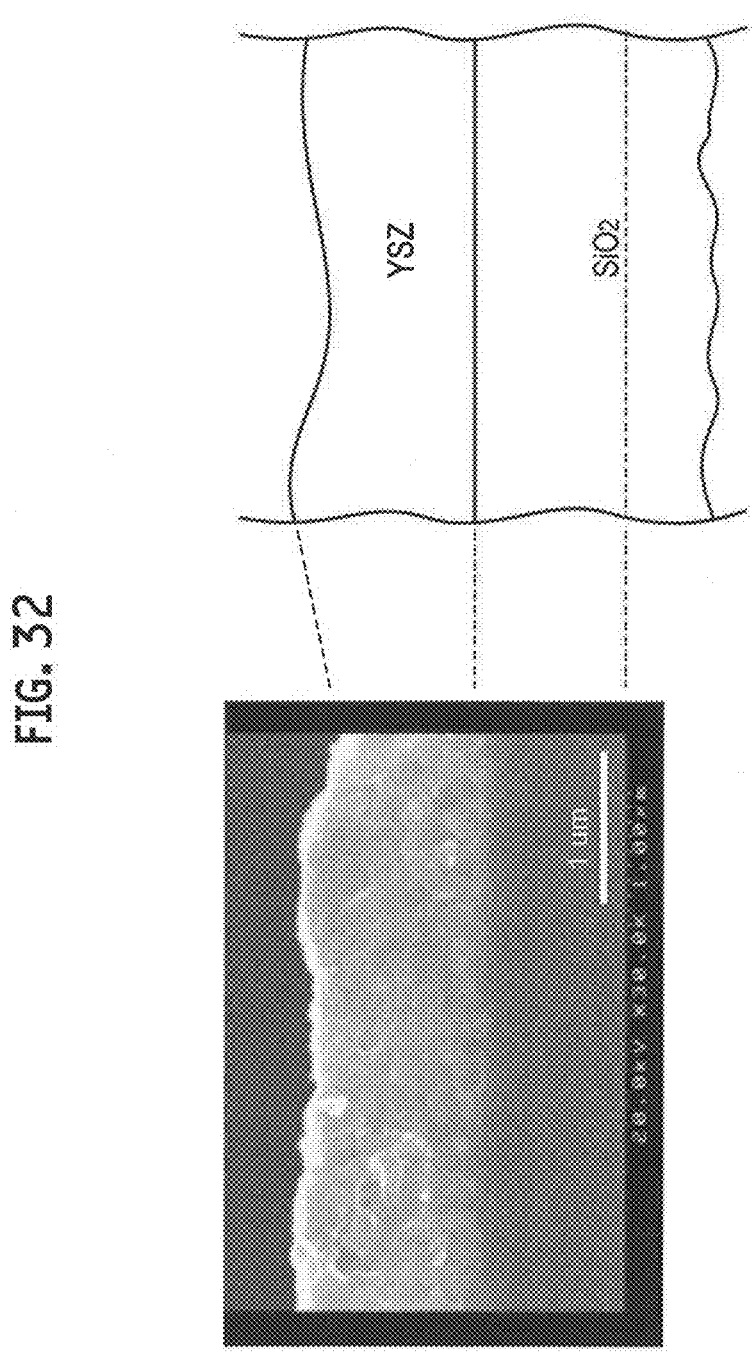
FIG. 32 shows an example of a cross-sectional Scanning Electron Microscope (SEM) photograph in a state where YSZ-10 wt % SiO$_2$ is annealed at 1300 degrees C., in the limiting-current type gas sensor according to the embodiments.

In formation of the solid electrolyte layer (YSZ) 4 of the limiting-current type gas sensor according to the embodiments, FIG. 31 shows an example of a cross-sectional SEM photograph in a state where YSZ-10 wt % $SiO_2$ is annealed at 1200 degrees C., and FIG. 32 shows an example of a cross-sectional SEM photograph in a state where YSZ-10 wt % $SiO_2$ is annealed at 1300 degrees C. In the embodiments, the solid electrolyte layer (YSZ) 4 is formed at approximately 1 μm in thickness on a silicon oxide film experimentally formed on the silicon substrate.

The solid electrolyte layer (YSZ) 4 is denser in the photograph (FIG. 32) in the case of the annealing temperature of 1300 degrees C., as compared with the photograph (FIG. 31) in the case of the annealing temperature of 1200 degrees C. Due to such densification of the solid electrolyte layer (YSZ) 4, the surface conduction component of the electric current can be reduced by one or more orders of magnitude. The surface-conduction current disclosed herein corresponds to electrical conduction which occurs sue to a chain reaction of Grotthhus mechanism of transferring protons from one water molecule to next water molecule on a water-adsorbed layer of an oxide surface, and thereby transporting oxonium ion $(H_3O)^+$ which is adsorbed on the surface along a direction of a chain reaction.

In the limiting-current type gas sensor according to the embodiments, by fabricating elements on the beam structure, the device heating unit can be made as a small area and a thin layer, and thereby achieving power consumption reduction.

Moreover, in the limiting-current type gas sensor according to the embodiments, the ionic conduction is improved and the surface conduction component is reduced by making the sensor portion as the vertical structure of the electrode/stabilized zirconia film/electrode, while the warpage of the beam structure at the time of heating and cooling is reduced, and durability thereof can be improved, by forming the low-thermal expansion insulating film on the uppermost surface.

Moreover, in the limiting-current type gas sensor according to the embodiments, Yttrium-Stabilized Zirconia (YSZ) can be formed by sputtering or printing. In particular, if printing is used, it can be inexpensively mass-produced. Moreover, in the YSZ, YSZ dense films can be formed on the silicon substrate by using a distributed process and by adding a sintering additive. Due to such densification, the surface conduction component can be reduced, and satisfactory limiting current characteristics can be appeared, and thereby the sensor sensitivity can be improved.

(Package)

Figure 33:
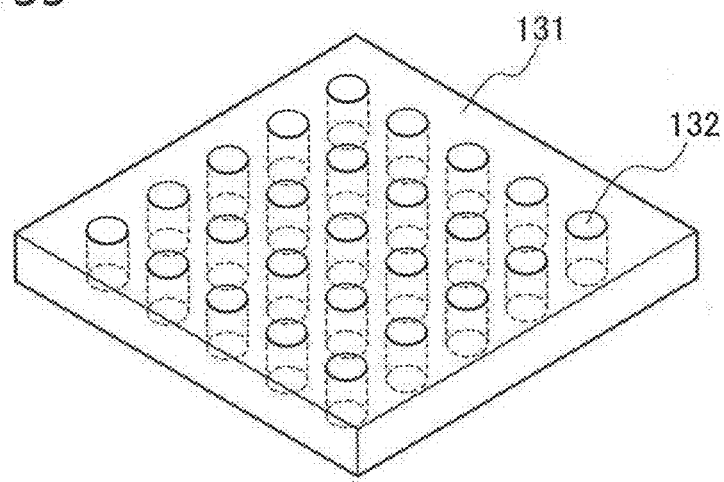
FIG. 33 is a schematic bird's-eye view configuration diagram showing a sealing cover of a package for housing the limiting-current type gas sensor according to the embodiments.

FIG. 33 shows a schematic bird's-eye view configuration showing a sealing cover 131 of a package for housing the limiting-current type gas sensor according to the embodiments. As shown in FIG. 33, a large number of through holes 132, through which gas can be passed but foreign substances cannot be passed, are formed in the sealing cover 131 of the package. Metal meshed, metal having small holes, porous ceramics, etc. are applicable to the sealing cover 131 of the package.

Figure 34:
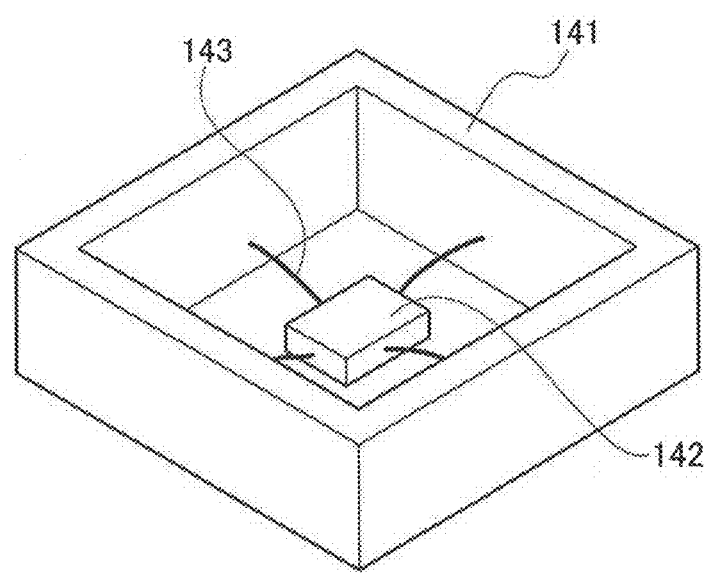
FIG. 34 is a schematic bird's-eye view configuration diagram showing a main unit of the package for housing the limiting-current type gas sensor according to the embodiments.

FIG. 34 shows a schematic bird's-eye view configuration showing a main unit 141 of a package for housing the limiting-current type gas sensor according to the embodiments. As shown in FIG. 34, a limiting-current type gas sensor chip 142 including a plurality of terminals is housed in the main unit 141 of the package, and is electrically connected with a plurality of bonding wires 143. The sealing cover 131 is covered on an upper part of the main unit 141 of the package, and then is mounted on the printed circuit board 101 etc. with a solder.

(Configuration Example of Sensor Node Using Energy Harvesting Power Supply)

Figure 35:
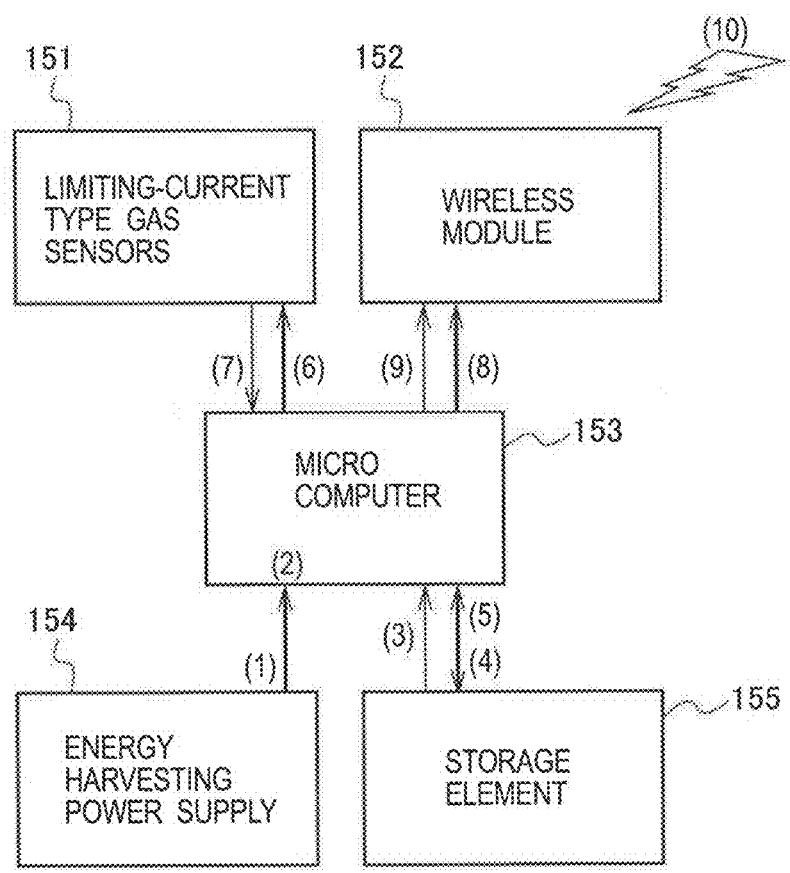
FIG. 35 is a schematic block configuration diagram showing the limiting-current type gas sensor according to the embodiments.

As shown in FIG. 35, the limiting-current type gas sensor (sensor node) according to the embodiments includes: a limiting-current type gas sensors 151; a wireless module 152; a microcomputer 153; an energy harvesting power supply 154; and a storage element 155. A configuration of the limiting-current type gas sensors 151 is as explained in the embodiments. The wireless module 152 is a module including an RF circuit etc. for transmitting and receiving radio frequency signals. The microcomputer 153 includes a management function of the energy harvesting power supply 154, and is configured to input the electric power from the energy harvesting power supply 154 to the limiting-current type gas sensors 151. At this time, the microcomputer 153 may input the electric power in accordance with a heater power profile for saving the power consumption in the limiting-current type gas sensors 151. For example, after the first electric power that is relatively large electric power is input only for the first time period T1, the second electric power that is relatively small electric power may input only for the second time period T2. Moreover, the data is read at the second time period T2, and then the input of electric power may be stopped only for the third time period T3 after the second time period T2 elapses. The energy harvesting power supply 154 harvests energies, e.g. a solar light, an illumination light, a vibration generated from machines, and a heat, thereby obtaining electric power. The storage element 155 is a lithium ion storage element etc. in which electric power can be electricity stored.

Hereinafter, operation of such a sensor node will now be explained. Firstly, as shown with the mark (1) in FIG. 35, the electric power from the energy harvesting power supply 154 is supplied to the microcomputer 153. Accordingly, the microcomputer 153 boosts voltage supplied from the energy harvesting power supply 154, as shown with the mark (2) in FIG. 35. Next, after reading the voltage of the storage element 155, as shown with the mark (3) in FIG. 35, the electric power is supplied to the storage element 155 and the electric power is extracted from the storage element 155 as shown with the marks (4) and (5) in FIG. 35. Next, the electric power is input to the limiting-current type gas sensors 151 on the basis of the heater power profile as shown with the mark (6) in FIG. 35, and then the data, such as sensor resistance, Pt resistance value, etc. is read out as shown with the mark (7) in FIG. 35. Next, the electric power is supplied to the wireless module 152 as shown with the mark (8) in FIG. 35, and then the data, such as sensor resistance, Pt resistance value, etc. is sent to the wireless module 152 as shown with the mark (9) in FIG. 35. Finally, as shown with the mark (10) in FIG. 35, the data, such as sensor resistance, Pt resistance value, etc. is wirelessly transmitted by the wireless module 152.

(Sensor Package)

Figure 36:
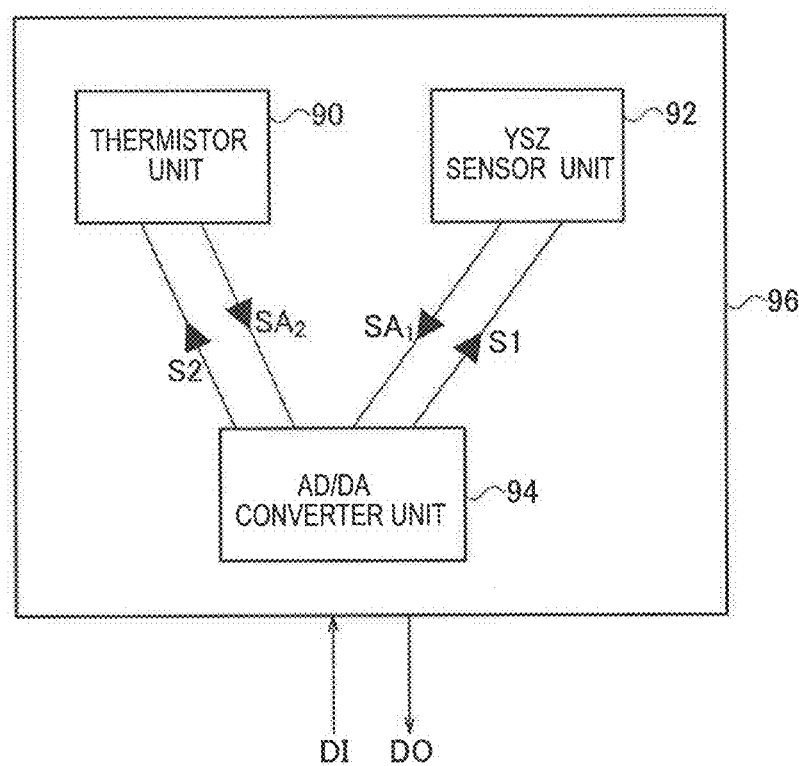
FIG. 36 is a schematic block configuration diagram showing a sensor package in which the limiting-current type gas sensor according to the embodiments is mounted.

FIG. 36 shows a schematic block configuration of a sensor package 96 in which the limiting-current type gas sensor according to the embodiments is mounted.

As shown in FIG. 36, the sensor package 96 in which the limiting-current type gas sensor according to the embodiments is mounted includes: a thermistor unit 90 for temperature sensors; a YSZ sensor unit 92 for humidity and oxygen sensors; an AD/DA converter unit 94 configured to receive analog information $SA_2$, $SA_1$ from the thermistor unit 90 and the YSZ sensor unit 92, and supplies control signals $S_2$, $S_1$ to the thermistor unit 90 and the YSZ sensor unit 92; and digital input/output signals DI, DO from the outside.

A Negative Temperature Coefficient (NTC) thermistor, a Positive Temperature Coefficient (PTC) thermistor, a ceramic PTC, a polymer PTC, a Critical Temperature Resistor (CTR) thermistor, etc. can be applied to the thermistor unit 90, for example. The limiting-current type gas sensor according to the embodiments can be applied to the YSZ sensor unit 92. Although Absolute Humidity (AH) and Relative Humidity (RH) are can also be measured by the YSZ sensor unit 92, since the temperature is used as a reference in particular for detection of the RH, temperature information detected by the thermistor unit 90 is required therefor.

(Sensor Network)

FIG. 37 shows a schematic block configuration of a sensor network to which the limiting-current type gas sensor according to the embodiments is applied. As shown in FIG. 37, the sensor network is a network interconnected to many sensors. Novel efforts using a sensor network in various fields, e.g. factories, medical care/health care, transport facilities, construction industries, agricultural facilities, and environmental management, have already been started. Since it is desired to use sensors with high durability in such fields, it is preferable to apply the limiting-current type gas sensor (for example, humidity sensor) according to the embodiments. Such a humidity sensor is excellent in durability by using zirconia. Accordingly, it is possible to provide the reliable sensor network.

As mentioned above, according to the embodiment, there can be provided: the limiting-current type gas sensor capable of reducing the surface-conduction current component and realizing low power consumption; the fabrication method of such a limiting-current type gas sensor; and the sensor network system.

Other Embodiments

As explained above, the embodiment has been described, as a disclosure including associated description and drawings to be construed as illustrative, not restrictive. This disclosure makes clear a variety of alternative embodiment, working examples, and operational techniques for those skilled in the art.

Such being the case, the embodiments described herein cover a variety of embodiments, whether described or not. For example, if Na Super Ionic Conductor (NASICON) instead of the zirconia is used for the solid electrolyte layer 4, it is possible to detect density of carbon dioxide.

INDUSTRIAL APPLICABILITY

The limiting-current type gas sensor according to the embodiments is applicable to an oxygen sensor and a humidity sensor. Such a sensor is also applicable to objects for an automobile exhaust gas and for sensor networks.

What is claimed is:

1. A limiting-current type gas sensor comprising:
   a substrate;
   a porous lower electrode disposed on the substrate;
   an insulating film disposed on the porous lower electrode;
   a solid electrolyte layer disposed on the porous lower electrode in an opening formed by patterning the insulating film, and further disposed on the insulating film surrounding the opening;
   a porous upper electrode disposed on the solid electrolyte layer so as to be opposite to the porous lower electrode, and so as to be disposed in a substantially vertical direction with respect to the substrate;
   a first low-thermal expansion film for stress relaxation disposed on the porous upper electrode;
   a second low-thermal expansion film for stress relaxation disposed on the porous lower electrode;
   a third low-thermal expansion film for stress relaxation disposed on the solid electrolyte layer;
   a first porous insulating film for suppressing warpage disposed on the porous upper electrode so as to extend over between the first low-thermal expansion film for stress relaxation and the third low-thermal expansion film for stress relaxation in a planar view; and
   a second porous insulating film for suppressing warpage disposed on the porous lower electrode so as to extend over the second low-thermal expansion film for stress relaxation and the third low-thermal expansion film for stress relaxation in a planar view, wherein
   the insulating film prevents contact between an edge face of the solid electrolyte layer and the porous lower electrode, such that an intake of oxygen (O) ions from the edge face of the solid electrolyte layer is suppressed, thereby reducing a surface-conduction current component between the porous upper electrode and the porous lower electrode.

2. The limiting-current type gas sensor according to claim 1, further comprising
   a detection circuit configured to detect a predetermined gas density in measured gas with a limiting current method by applying voltage between the porous upper electrode and the porous lower electrode.

3. The limiting-current type gas sensor according to claim 1, wherein the substrate comprises a micro heater.

4. The limiting-current type gas sensor according to claim 1, wherein
   the porous lower electrode and the porous upper electrode comprises a Pt electrode formed of a method selected from a group consisting of printing, vacuum evaporation, and sputtering.

5. The limiting-current type gas sensor according to claim 1, wherein
   the insulating film comprises one selected from a group consisting of $Al_2O_3$, $Al_2O_3$—$SiO_2$, YSZ—$SiO_2$ and YSZ—$Al_2O_3$.

6. The limiting-current type gas sensor according to claim 1, wherein
   the solid electrolyte layer comprises a stabilized zirconia film, the stabilized zirconia film containing at least one selected from a group consisting of YSZ, YSZ—$SiO_2$, or the YSZ—$Al_2O_3$.

7. The limiting-current type gas sensor according to claim 1, wherein
   a film density of each of the first low-thermal expansion film for stress relaxation, the second low-thermal expansion film for stress relaxation, and the third low-thermal expansion film for stress relaxation can be adjusted in accordance with a gas volume to be detected.

8. The limiting-current type gas sensor according to claim 7, wherein
   the first low-thermal expansion film for stress relaxation, the second low-thermal expansion film for stress relaxation, and the third low-thermal expansion film for stress relaxation comprise one selected from a group consisting of a dense film, a porous film, and a composite films of the dense film and the porous film.

9. The limiting-current type gas sensor according to claim 7, wherein
   the first low-thermal expansion film for stress relaxation, the second low-thermal expansion film for stress relaxation, and the third low-thermal expansion film for stress relaxation comprise a material containing at least one selected from a group consisting of $SiO_2$, $Al_2O_3$, YSZ, and mullite.

10. The limiting-current type gas sensor according to claim 1, wherein
    the first porous insulating film for suppressing warpage and the second porous insulating film for suppressing warpage comprise a material containing at least one selected from a group consisting of $SiO_2$, $Al_2O_3$, YSZ, and mullite.

11. The limiting-current type gas sensor according to claim 1, further comprising a gas intake film disposed on the substrate, wherein
    the porous lower electrode is disposed on the gas intake film.

12. The limiting-current type gas sensor according to claim 11, wherein
    the gas intake film comprises a porous film, the porous film containing one selected from a group consisting of $Al_2O_3$, $Al_2O_3$—$SiO_2$, YSZ—$SiO_2$ and YSZ—$Al_2O_3$.

13. The limiting-current type gas sensor according to claim 2, wherein the detection circuit detects oxygen density on the basis of limiting current.

14. The limiting-current type gas sensor according to claim 2, wherein the detection circuit detects vapor density on the basis of limiting current.

15. A fabrication method of a limiting-current type gas sensor, the fabrication method comprising:
    forming a porous lower electrode on a substrate;
    forming an insulating film on the porous lower electrode;
    patterning the insulating film in order to form an opening;
    forming a solid electrolyte layer on the porous lower electrode in the opening and on the insulating film surrounding the opening;

forming a porous upper electrode on the solid electrolyte layer so as to be opposite to the porous lower electrode, and so as to be disposed in a substantially vertical direction with respect to the substrate;

forming a first low-thermal expansion film for stress relaxation on the porous upper electrode, forming a second low-thermal expansion film for stress relaxation on the porous lower electrode, and forming a third low-thermal expansion film for stress relaxation on the solid electrolyte layer;

forming a first porous insulating film for suppressing warpage on the porous upper electrode so as to extend over between the first low-thermal expansion film for stress relaxation and the third low-thermal expansion film for stress relaxation in a planar view; and forming a second porous insulating film for suppressing warpage on the porous lower electrode so as to extend over the second low-thermal expansion film for stress relaxation and the third low-thermal expansion film for stress relaxation in a planar view, wherein the insulating film prevents contact between an edge face of the solid electrolyte layer and the porous lower electrode, such that an intake of oxygen (O) ions from the edge face of the solid electrolyte layer is suppressed, thereby reducing a surface-conduction current component between the porous upper electrode and the porous lower electrode.

16. A sensor network system comprising a limiting-current type gas sensor, wherein the limiting-current type gas sensor comprises:

a substrate;

a porous lower electrode disposed on the substrate;

an insulating film disposed on the porous lower electrode;

a solid electrolyte layer disposed on the porous lower electrode in an opening formed by patterning the insulating film, and further disposed on the insulating film surrounding the opening;

a porous upper electrode disposed on the solid electrolyte layer so as to be opposite to the porous lower electrode, and so as to be disposed in a substantially vertical direction with respect to the substrate;

a first low-thermal expansion film for stress relaxation disposed on the porous upper electrode;

a second low-thermal expansion film for stress relaxation disposed on the porous lower electrode;

a third low-thermal expansion film for stress relaxation disposed on the solid electrolyte layer;

a first porous insulating film for suppressing warpage disposed on the porous upper electrode so as to extend over between the first low-thermal expansion film for stress relaxation and the third low-thermal expansion film for stress relaxation in a planar view; and a second porous insulating film for suppressing warpage disposed on the porous lower electrode so as to extend over the second low-thermal expansion film for stress relaxation and the third low-thermal expansion film for stress relaxation in a planar view, wherein the insulating film prevents contact between an edge face of the solid electrolyte layer and the porous lower electrode, such that an intake of oxygen (O) ions from the edge face of the solid electrolyte layer is suppressed, thereby reducing a surface-conduction current component between the porous upper electrode and the porous lower electrode.

\* \* \* \* \*